United States Patent
Miyazaki et al.

(10) Patent No.: US 8,251,954 B2
(45) Date of Patent: Aug. 28, 2012

(54) FLUID TRANSPORTATION SYSTEM AND METHOD OF SETTING FLUID EJECTION AMOUNT

(75) Inventors: Hajime Miyazaki, Nagano (JP); Kazuo Kawasumi, Nagano (JP)

(73) Assignee: Seiko Epson Corporation (JP)

( * ) Notice: Subject to any disclaimer, the term of this patent is extended or adjusted under 35 U.S.C. 154(b) by 809 days.

(21) Appl. No.: 11/919,479

(22) PCT Filed: Apr. 24, 2006

(86) PCT No.: PCT/JP2006/309068
§ 371 (c)(1),
(2), (4) Date: Oct. 26, 2007

(87) PCT Pub. No.: WO2006/118285
PCT Pub. Date: Nov. 9, 2006

(65) Prior Publication Data
US 2009/0312708 A1    Dec. 17, 2009

(30) Foreign Application Priority Data

Apr. 27, 2005  (JP) .................. 2005-129082
May 10, 2005  (JP) .................. 2005-136920

(51) Int. Cl.
A61M 31/00 (2006.01)
(52) U.S. Cl. ........................................ 604/151
(58) Field of Classification Search ........... 604/151; 417/12, 212, 213
See application file for complete search history.

(56) References Cited

U.S. PATENT DOCUMENTS

| 3,737,251 | A | | 6/1973 | Berman et al. |
| 5,083,908 | A | | 1/1992 | Gagnebin et al. |
| 5,171,132 | A | * | 12/1992 | Miyazaki et al. .......... 417/413.1 |
| 5,239,319 | A | * | 8/1993 | Miyazaki et al. ............ 340/679 |
| 5,582,593 | A | * | 12/1996 | Hultman ....................... 604/65 |
| 5,764,034 | A | | 6/1998 | Bowman et al. |
| 6,790,198 | B1 | * | 9/2004 | White et al. ................. 604/151 |
| 7,069,059 | B2 | | 6/2006 | Osawa |
| 7,121,744 | B2 | | 10/2006 | Yamauchi et al. |
| 7,139,488 | B1 | | 11/2006 | Mituhashi |

(Continued)

FOREIGN PATENT DOCUMENTS

JP        58-070080       4/1983
(Continued)

OTHER PUBLICATIONS

International Search Report for PCT/JP2006/309068, dated Aug. 21, 2006 (in English and Japanese).

(Continued)

Primary Examiner — Nicholas Lucchesi
Assistant Examiner — Aarti B Berdichevsky
(74) Attorney, Agent, or Firm — Harness, Dickey & Pierce, P.L.C.

(57) ABSTRACT

A fluid transportation system includes a fluid transportation device housing a flexible tube, a pump unit for ejecting a fluid by squeezing the tube, a communication section, and a battery, an ejection data processing device having an input device for inputting to the fluid transportation device a driving condition for ejecting a desired ejection amount of the fluid, a display section for displaying at least the driving condition, and a communication device for connecting the fluid transportation device and the ejection data processing device to each other, wherein the fluid transportation device is driven based on the driving condition input from the ejection data processing device.

18 Claims, 15 Drawing Sheets

U.S. PATENT DOCUMENTS

| | | | |
|---|---|---|---|
| 7,407,490 B2 | 8/2008 | Bendsen et al. | |
| 7,762,788 B2 * | 7/2010 | Miyazaki et al. | 417/212 |
| 2002/0063936 A1 | 5/2002 | Mituhashi | |
| 2003/0179531 A1 | 9/2003 | Yamaguchi | |
| 2004/0176984 A1 * | 9/2004 | White et al. | 705/2 |
| 2006/0002799 A1 * | 1/2006 | Schann et al. | 417/1 |
| 2006/0270916 A1 * | 11/2006 | Skwarek et al. | 600/300 |
| 2006/0271020 A1 * | 11/2006 | Huang et al. | 604/890.1 |
| 2009/0312708 A1 | 12/2009 | Miyazaki et al. | |

FOREIGN PATENT DOCUMENTS

| | | |
|---|---|---|
| JP | 58-198878 | 11/1983 |
| JP | 62-183770 | 8/1987 |
| JP | 04-186898 | 7/1992 |
| JP | 05-241994 | 9/1993 |
| JP | 06-154321 A | 6/1994 |
| JP | 07-059853 A | 3/1995 |
| JP | 7-059853 A | 3/1995 |
| JP | 08-057047 A | 3/1996 |
| JP | 10-057480 A | 3/1998 |
| JP | 11-161389 | 6/1999 |
| JP | 11-319083 | 11/1999 |
| JP | 11-319083 A | 11/1999 |
| JP | 11-342199 A | 12/1999 |
| JP | 2000-042103 | 2/2000 |
| JP | 3177742 | 4/2001 |
| JP | P3177742 B2 | 4/2001 |
| JP | 2001-321331 A | 11/2001 |
| JP | 2002-506514 | 2/2002 |
| JP | 2002-085556 | 3/2002 |
| JP | 2002-523149 | 7/2002 |
| JP | 2003-143059 | 5/2003 |
| JP | 2003-281036 | 10/2003 |
| JP | 2003-329895 | 11/2003 |
| JP | 2004-298610 A | 10/2004 |
| JP | P2004-532670 A | 10/2004 |
| JP | 2004-313383 A | 11/2004 |
| JP | 2005-070832 | 3/2005 |
| JP | 2005-510305 | 4/2005 |
| JP | P2005-514175 A | 5/2005 |
| JP | 2007-075627 | 3/2007 |
| JP | 4557789 | 7/2010 |
| WO | WO 00-10628 | 3/2000 |
| WO | WO-02/068015 A2 | 9/2002 |
| WO | WO-03/024385 A1 | 3/2003 |
| WO | WO-03/059418 A1 | 7/2003 |
| WO | WO2004-012043 | 2/2004 |

OTHER PUBLICATIONS

Japanese Office Action with English Translation for JP 2008-125601 dated Sep. 13, 2011 (6 pages).

* cited by examiner

| Fundamental data setting (module: TEST1) | |
|---|---|
| Stepping motor driving pulse frequency [Hz]: | 64 |
| Reference value of micro pump ejection amount [μl/revolution]: | 9.869 |
| Correction coefficient []: | 1.000 |
| Micro pump ejection amount [μl/revolution]: | 9.869 |
| Upper limit value of maximum ejection rate [μl/H]: | No upper limitation |
| Initial ejection rate [μl/H]: | 25 |
| Initial driving period [s]: | 30 |
| Stepping motor pulse width [ms]: | 6.84 |
| Stepping motor speed reduction ratio []: | 19300 |
| Battery capacity [mAH]: | 45.0 |
| Safety ratio []: | 0.80 |
| Stepping motor current consumption [μA/step]: | 3.0 |
| CPU in-operation current consumption [μA]: | 1.7 |
| Power supply voltage detection circuit (SVD): | ○ OFF   ● ON |
| Power supply voltage detection circuit (SVD) detection interval [min]: | 1 |
| Power supply voltage detection circuit (SVD) detection voltage [V]: | 1.13 |

Register        Cancel

FIG.16

Micro pump module name & code input

Enter micro pump module name:

MicroPumpNo1

Enter micro pump module code:

0503311000

OK        Cancel

FIG.17

| Ejection data setting MULTIPLE No. 1 (module: TEST1) | |
|---|---|
| Maximum settable ejection rate [µl/H]: | 15 |
| Ejection rate setting [µl/H]: | 5.0 |
| Maximum settable ejection period [H]: | 1674 |
| Maximum ejection amount [µl]: | 8370.0 |
| Ejection period setting [H]: | 1.0 |
| Ejection amount of No. 1 [µl]: | 5.00 |
| Total ejection amount [µl]: | 5.00 |

Register    Undo    Cancel

FIG.26

| Micro pump ejection information (module: TEST1) | |
|---|---|
| Micro pump operation data: | Single data |
| Micro pump stopping reason: | Time-out |
| Micro pump driving period [H]: | 0.0 |
| Micro pump total ejection amount [µl]: | 0.00 |

# FLUID TRANSPORTATION SYSTEM AND METHOD OF SETTING FLUID EJECTION AMOUNT

CROSS-REFERENCE TO RELATED APPLICATIONS

This application is a National Stage of International Application No. PCT/JP2006/309068, filed Apr. 24, 2006, claiming priority to Japanese Patent Application No. 2005-136920, filed May 10, 2005, and to Japanese Patent Application No. 2005-129082, filed Apr. 27, 2005. The entire disclosures of each of the above applications are incorporated herein by reference.

BACKGROUND

1. Technical Field

The present invention relates to a fluid transportation system and a method of setting a fluid ejection amount in the fluid transportation system. For details, the present invention relates to a fluid transportation system equipped with a miniature fluid transportation device, an ejection data processing device, and a communication device, and to a fluid ejection amount setting method for accurately setting an amount of fluid ejection.

2. Related Art

In recent years, application of a miniature pump, which is used for continuously administering a small amount of medicinal liquid to a patient in a form of a slow current, to treatment has been studied.

For example, as first related art, there is cited a miniature peristaltic pump device suitable for attachment to a human body for slowly and continuously injecting it with an aqueous medicinal liquid in which a rotor of the pump is attached to a shaft, the rotor being provided with a plurality of rollers disposed to be evenly distributed on the periphery of the shaft, the rollers perform rotational movement while rotating along a flexible tube to press the tube against a backing surrounding the tube in a circular range with a predetermined length, thus performing suction and ejection of a fluid such as a medicinal liquid.

There is known such a miniature peristaltic pump device provided with a stepping motor as a power supply driven at a rotational speed set previously by a block IC having a control circuit, thus achieving a desired amount of ejection (Japanese Patent No. 3177742).

Further, as second related art, there is known a peristaltic pump device provided with a miniature peristaltic pump, an input switch for setting the fluid ejection amount of the miniature peristaltic pump to a plurality of levels and setting the fluid ejection amount by selecting from the plurality of setting levels, and a display section disposed on a housing (specification of U.S. Pat. No. 3,737,251).

In the invention according to the first related art described above, although the ejection amount of the medicinal liquid and so on can be set or changed in accordance with the number of frequency divider stages for receiving a signal supplied from a time base, a reduction ratio of a gear mechanism, or a type of a motor used therefor, it is required to be manufactured with the setting condition determined previously. However, the ejection condition once determined is unchangeable, and there arises a problem that it is difficult to set the fluid ejection amount while arbitrarily changing the form of usage or the condition of administering the medicinal liquid.

Further, in the invention according to the second related art, although the switch for adjusting the ejection amount of the fluid, the display section, and the peristaltic pump are disposed on the housing so as to allow the adjustment of the ejection amount, downsizing is difficult with such a configuration in which the miniature peristaltic pump, the switch, and the display section are mounted on the housing, and consequently, it can hardly be mounted inside a body of a small animal for the purpose of developing a new drug and so on.

Further, the inventions according to the first and second related art described above relate to a peristaltic pump for ejecting a liquid by squeezing a tube, and consequently, an ejection amount of the liquid is proportional to the square (the cross-sectional area) of the diameter of a liquid flow section of the tube. Further, there might be caused a variation in diameter of the tube having flexibility in the manufacturing process thereof. In particular, it is well known that there is a variation among production lots.

Such a variation in diameter of the tube causes a variation in ejection amount of the liquid, and in particular in the case of the application to administration of a medicinal liquid, the variation in tube diameter is a substantive issue because a small amount of ejection is continuously performed and accurate ejection amount control is required. However, in the first and second related art described above, there is a problem that the accurate adjustment of the ejection amount in consideration of the variation in tube diameter can hardly be performed.

Further, it is conceivable that it does not cope with a variation in remaining power or voltage of a battery as a power supply, improper driving of the pump, shortage of drive period, and so on, and consequently, it is inferred that a significant problem unable to be left unsolved arises in the case of administration of a medicinal liquid.

SUMMARY

In view of the above problems, an advantage of some aspects of the present invention is to provide a fluid transportation system equipped with a communication device and capable of accurately setting and controlling a small amount of ejection of the fluid among a fluid transportation device and an ejection data processing device and a method of setting an accurate ejection amount of a fluid.

According to an aspect of the invention there is provided a fluid transportation system including a fluid transportation device housing a flexible tube, a pump unit for ejecting a fluid by squeezing the tube, a communication section, and a battery, an ejection data processing device having an input device for inputting to the fluid transportation device a driving condition for ejecting a desired ejection amount of the fluid, a display section for displaying at least the driving condition, and a communication device for connecting the fluid transportation device and the ejection data processing device to each other, wherein the fluid transportation device is driven based on the driving condition input from the ejection data processing device.

According to this aspect of the invention, the fluid transportation system is composed of the fluid transportation device, the ejection data processing device, and the communication device, and inputs the driving condition data of the fluid transportation device from the input device of the ejection data processing device to drive the fluid transportation device based on the driving condition, thus the setting of the ejection rate (the ejection amount) can be performed in the ejection data processing device, and the user-friendly fluid transportation system can be provided.

Further, since the fluid transportation system according to this aspect of the invention can display the driving condition data and the driving status data of the fluid transportation device on the display section of the ejection data processing device, it is preferable for controlling the fluid transportation system of a fluid such as a medicinal liquid to which accurate flow rate control is required.

Further, since the fluid transportation device and the ejection data processing device are connected by the communication device, it is enough for the fluid transportation device to implement only the functions directly related to the fluid transportation, thus the fluid transportation device can be downsized.

Further, in this aspect of the invention, the communication device is a wireless communication device, and the communication device includes at least an antenna and a transmission/reception switcher, and the communication section includes an antenna and a transmission/reception switcher.

According to this configuration, since the fluid transportation device and the ejection data processing device can separately be configured, the fluid transportation device can be downsized by simplifying the outer shape thereof, and in addition, the restriction in the use environment relating to the communication can be eased because the communication is possible even if a partition or the like exists between the fluid transportation device and the ejection data processing device. Further, since the transmission/reception is possible between the fluid transportation device and the ejection data processing device, the driving condition can be input from the ejection data processing device to the fluid transportation device, and the ejection information can be input from the fluid transportation device to the ejection data processing device, thus the ejection control of the fluid can appropriately be performed.

Further, the communication device is an optical communication device, the communication device includes at least a light receiving element, a light emitting element, a light reception control circuit, and a light emission control circuit, and the communication section includes a light emitting element and a light receiving element respectively opposed to the light receiving element and the light emitting element, a light emission control circuit, and a light reception control circuit.

Here, as the optical communication device, an infrared communication device used for remote-control system and so on can be used, for example.

Although the optical communication method has a little additional restriction in use environment relating to the communication in comparison with the wireless communication method using a radio wave, the simple configuration thereof provides expectation of cost reduction.

Further, the communication device is a wired communication device, and the fluid transportation system according to this aspect of the invention further includes a seal member formed of an elastic body and attached to a chassis of the fluid transportation device, a first connection terminal provided to the seal member and for connecting the inside and the outside of the seal member, and a second connection terminal provided to the communication device, wherein the first and second connection terminals are connected to each other when the fluid transportation device is mounted on the communication device, thereby connecting the communication device and the fluid transportation device to each other.

According to this structure, the fluid transportation device and the communication device are each provided with the first connection terminal and the second connection terminal. By mounting the fluid transportation device on the communication device, the first and second connection terminals are respectively connected to each other, thus enabling the communication therebetween. Therefore, reliability of communication can be improved with the simple structure.

Further, by detaching the fluid transportation device from the communication device, the connection between the fluid transportation device and the communication device is broken. Further, since the fluid transportation device can be driven by itself, an advantage of being hardly influenced by the external noises can also be obtained.

Further, the seal member is mainly composed of an outer periphery fixing section fixed to the chassis of the fluid transportation device, a connection terminal fixing section to which the first connection terminal is implanted to stand, an elastic section connecting the outer periphery fixing section and the connection terminal fixing section.

The seal member has shapes for increasing the rigidity in the outer peripheral section and the connection terminal fixing sections, and has elasticity in other sections. Therefore, when the fluid transportation device is mounted on the communication device, the elastic section is distorted to allow connection between the first connection terminals and the second connection terminals, respectively. Further, when separating the communication device and the fluid transportation device from each other, the connection is released by restoring the first connection terminals to the initial position by means of the elasticity of the elastic section. Thus, the connection and the release of the connection between the communication device and the fluid transportation device can be performed with the simple structure.

Further, the communication device is a wired communication device, and the fluid transportation system according to this aspect of the invention further includes a seal member formed of an elastic body and attached to a chassis of the fluid transportation device, and a connection terminal implanted to the communication device to stand, and provided with a needle section formed at an end of the connection terminal, wherein the needle section pierces the seal member and the connection terminal is connected to the connection terminal of the fluid transportation device when the fluid transportation device is mounted on the communication device, and when the fluid transportation device is detached from the communication device, the connection is released and the seal member is closed by the elasticity of the seal member.

According to such a structure, when the fluid transportation device is mounted on the communication device, the needle section of the connection terminal pierces and penetrates the seal member to connect the communication device and the fluid transportation device to each other, and when they are separated, the connection is released, and further the seal member is closed by the elasticity of the seal member itself, and consequently, the fluid transportation device with further simplified structure can be realized.

Further, in this aspect of the invention, a chassis forming the fluid transportation device has a projection-less outer shape, and the chassis and the tube are made of a biocompatible material.

According to this configuration, since there is no projection in the outer shape of the chassis of the fluid transportation device, it is possible to safely mount the fluid transportation device inside or outside the living body, and further, it is made of a biocompatible material, thus the development of rejection, allergic symptoms, and so on can be alleviated.

Further, the fluid transportation device is sealed except an inlet and outlet of the tube.

The fluid transportation device houses the drive section, the drive control section, the communication section, the power supply and soon as described above, and consequently, is sensitive to moisture, dust, or the like. Therefore, by forming the fluid transportation device to have a sealed structure, there can be obtained an advantage that infiltration of moisture, dust, and so on can be eliminated, infiltration of blood or the body fluid can be prevented, a predetermined driving performance is maintained, and highly reliable fluid transportation can be continued if the fluid transportation device is mounted inside the living body. Further, the operation in the different kind of liquid from the target liquid of the transportation becomes possible.

Further, the pump unit includes at least a stepping motor, a gear train for reducing the rotation of the stepping motor, a drive control circuit for controlling a drive of the stepping motor, and the drive control circuit includes a drive pulse setting section for storing a plurality of driving conditions of the stepping motor, and a timer for counting a driving period of the stepping motor, drives the pump unit based on the driving condition input from the ejection data processing device, and stops the pump unit after a predetermined period of time has elapsed.

As described above, it is possible to previously setting a plurality kinds of driving condition of the stepping motor, to select the optimal condition in accordance with the ejection amount of the fluid per unit time (the ejection rate), the driving load of the fluid transportation device, and the battery capacity, and to perform driving with the selected condition.

Further, since the drive control circuit is provided with a timer, after the fluid transportation device is started by the ejection data processing device, the fluid transportation device can be stopped by the instruction of the drive control circuit when a predetermined driving period (the total ejection amount) has been reached.

Further, the reduction ratio of the gear train can be changed by changing an arrangement of the gears of the gear train.

By adopting the structure capable of changing the reduction rate of the gear train, the ejection rate in the range difficult to be set by the driving condition of the stepping motor described above can be selected, and in addition, the output torque of the end of the gear train can be increased by increasing the reduction ratio of the gear train to correspond to the case in which the load of the pump unit becomes large, thus it becomes possible to meet the various needs of the user for the specifications.

Further, the driving condition input to the fluid transportation device includes fundamental data set initially and ejection data of individual fluid transportation device as a driving target set prior to driving the pump unit, and the fundamental data and the ejection data are set separately.

The fundamental data denotes, for example, the driving condition common to the fluid transportation devices, and the ejection data denotes the driving condition corresponding to the actual use conditions and unique to the individual fluid transportation device.

As described above, by setting the fundamental data and the ejection data separately, setting errors and inputting errors can be eliminated.

On this occasion, the ejection data is set in accordance with an individual difference in the diameter of a fluid flowing section of the tube, thereby controlling the ejection amount of the fluid.

In the fluid transportation apparatuses for transporting (emitting) the fluid by squeezing the tube, the ejection amount of the fluid is proportional to the rotational speed of the stepping motor and the square (the cross-sectional area) of the diameter (hereinafter also referred to simply as a diameter) of the fluid flowing section of the tube. In the rotational speed of the stepping motor, there is caused no difference among the individual fluid transportation apparatuses by previously setting the rotational speed. However, it is known that in the diameter of the tube, there is caused a variation in the manufacturing process, and in particular the difference among the production lots is often caused.

Therefore, in the case in which a small amount of fluid is transported, the influence of the diameter difference of the tubes to the ejection amount becomes a substantive level. Therefore, by setting the ejection data in accordance with the diameter of the tube, the accurate ejection amount free from the variation in the diameter of the tube can be assured.

Further, in this aspect of the invention, a correction coefficient is calculated from a ratio between a reference value of the diameter of the fluid flowing section of the tube in the driving condition of the fluid transportation device as a reference and the diameter of the fluid flowing section of the fluid transportation device as the driving target, and the ejection data of the fluid transportation device is set in accordance with the correction coefficient to correct the ejection amount of the fluid of the fluid transportation device so as to be the same as the ejection amount of the fluid of the fluid transportation device as the reference.

As described above, although the variation in the diameter of the tube causes the ejection amount of the fluid to vary, since the individual correction coefficient is calculated from the ratio between the diameter of the reference tube and the diameter of the target tube to set the ejection data individually to the fluid transportation device to be the driving target, the accurate ejection amount free from the influence of the variation in the diameter of the tube can be obtained.

Further, the fluid transportation device is driven with an initial driving term in which the fluid transportation device is driven based on an initial ejection rate and an initial driving period included in the fundamental data until the ejection of the fluid is started, and an effective driving term following the initial driving term.

Here, the effective driving term denotes in, for example, administration of the medicinal liquid, the driving term of the fluid transportation device to be controlled in which the medicinal liquid can constantly be transported.

Although described in detail in the embodiment section, the fluid transportation device of this aspect of the invention is a pump unit for performing ejection by squeezing the tube, and has a structure in which the roller is separated from the pressing shaft immediately after the structure is assembled, then the roller moves to the position for pressing the pressing shaft in the initial driving term, and the ejection of the fluid begins thereafter. Before ejection, deformation of the tube caused by continuously pressing a specific position of the tube of the fluid is eliminated, and in the effective driving term, a predetermined ejection amount can stably be obtained.

Further, the drive control circuit further includes a power supply voltage detection circuit for detecting a voltage of the battery, and the drive control circuit stops the fluid transportation device when a detection value of the power supply voltage detection circuit becomes lower than a predetermined driving voltage of the pump unit.

The voltage of the battery is lowered when the remaining power comes closer to the exhaustion. Further, it is conceivable that the variation in voltage specification exists depending on the battery. When the battery voltage is lowered, normal driving of the stepping motor might become difficult, and the predetermined ejection amount might hardly be obtained. However, by detecting the battery voltage by the power supply voltage detection circuit to stop driving the stepping motor when the battery voltage becomes lower than the drive voltage in the range in which the pump unit operates normally, the ejection amount of the fluid can be controlled.

Further, the ejection data processing device includes a section for selecting one of a single driving mode for driving the pump unit with a single kind of ejection data, and a multiple driving mode for driving the pump unit with a plurality of kinds of ejection data while switching the plurality of kinds of ejection data.

As described above, in the fluid transportation device of this aspect of the invention, in addition to the single driving mode for keeping one kind of ejection data, the one fluid transportation apparatus can be driven while switching a plurality of kinds of ejection data (driving conditions). For example, such a driving mode becomes possible that the ejection rate in one hour after commencement of the driving is set high, the ejection rate in the next one hour is set lower, and in the next one hour the ejection rate is restored to the ejection rate in the beginning of the driving. Thus, assuming that a living-body test for a development of a new drug is executed, the relationship between the administration of the medicinal liquid and the administration rate can sensitively be acknowledged.

Further, in this aspect of the invention, ejection information data obtained when the fluid transportation device is driven is input from the fluid transportation device to the ejection data processing device via the communication device.

Such driving information data is input to the ejection data processing device via the communication device. Thus, the set ejection data and the ejection information data in actual driving can be compared, the driving management of the fluid transportation device, namely the management of the ejection amount can appropriately be performed by adjusting the ejection amount according to needs referring to the ejection information data.

Further, the ejection information data includes at least a stopping reason and a driving period of the fluid transportation device.

Since such ejection information data can be confirmed by the ejection data processing device, regarding the stopping reason of the fluid transportation device, whether the battery voltage has been lowered or other driving errors have occurred in the fluid transportation device can be discriminated. Further, since the total ejection amount can be calculated from the set ejection data and the actual driving period, the management of the fluid transportation device can appropriately be performed.

Further, according to another aspect of the invention, there is provided a method of setting an ejection amount of a fluid including the steps of providing a fluid transportation system including a fluid transportation device housing a flexible tube, a pump unit for ejecting a fluid by squeezing the tube, a communication section, and a power supply, an ejection data processing device having an input device for inputting to the fluid transportation device a driving condition for ejecting a desired ejection amount of the fluid, a display section for displaying at least the driving condition, and a communication device for connecting the fluid transportation device and the ejection data processing device to each other, driving the fluid transportation device based on the driving condition input from the ejection data processing device, wherein the driving condition data input to the fluid transportation device includes fundamental data set initially and ejection data of the individual fluid transportation device as a driving target set at execution of the driving, and the driving step includes the steps of allowing a provider of the fluid transportation system to set the fundamental data by operating the individual ejection data processing device, and allowing a user of the fluid transportation system to set the ejection data by operating the individual ejection data processing device.

According to this aspect of the invention, the configuration is that the fundamental data relating to the common specifications of the fluid transportation devices is set by the provider of the fluid transportation system, while the ejection data corresponding to the actual use requirement of the fluid transportation device is set by the user of the fluid transportation system. Therefore, the user of the fluid transportation system is not allowed to modify the fundamental data, and further, the provider of the fluid transportation system is not allowed to modify the ejection data. Therefore, the provider of the fluid transportation system and the user of the fluid transportation system can easily perform necessary condition setting from the respective standpoints, and it can be prevented that different setting from the requirement is made by mistake.

Further, the method of setting an ejection amount of a fluid of this aspect of the invention described above further includes the steps of setting previously a reference value of a diameter of a fluid flowing section of the tube in the driving condition of the fluid transportation device as a reference, measuring the diameter of the fluid flowing section of the tube of the fluid transportation device as a driving target, calculating a correction coefficient from a ratio between the reference value of the diameter of the tube and the diameter of the tube of the fluid transportation device as the driving target, and setting the ejection data of the fluid transportation device corresponding to the correction coefficient, thereby adjusting the ejection amount of the fluid of the fluid transportation device so as to be the same as the ejection amount of the fluid of the fluid transportation device as the reference.

Thus, since the individual correction coefficient is calculated from the ratio between the reference tube diameter and the diameter of the tube as the driving target, and the ejection data is set for each of the fluid transportation apparatuses to be the driving target, the accurate ejection amount free from the influence of the variation in the diameter of the tube can be obtained.

The present invention can be applied to the fluid transportation system for administering a medicinal liquid, but not limited thereto, and can also be applied in various mechanical apparatuses to transportation of fluid such as water, a salt solution, a medicinal liquid, an oil, an aromatic liquid, ink, or a gas while being mounted inside or outside the apparatus.

BRIEF DESCRIPTION OF THE DRAWINGS

The invention will now be described with reference to the accompanying drawings, wherein like numbers refer to like elements.

FIG. 16 is an explanatory diagram showing "fundamental data setup screen" according to one embodiment of the invention.

FIG. 17 is an explanatory diagram showing "micro pump module name and code input screen" according to one embodiment of the invention.

FIG. 26 is an explanatory diagram showing "ejection data setup (multiple No. 1) screen" according to one embodiment of the invention.

FIG. 27 is an explanatory diagram of "micro pump ejection information screen" according to one embodiment of the invention.

DESCRIPTION OF EXEMPLARY EMBODIMENTS

Hereinafter, a fluid transportation system and a method of setting an ejection amount of a fluid by the fluid transportation system according to an embodiment of the invention will be explained. It should be noted that the embodiments described below are each nothing more than one embodiment of the invention, and consequently, the invention is not limited thereto.

Firstly, a first embodiment of the invention will be described.

Figure 1:
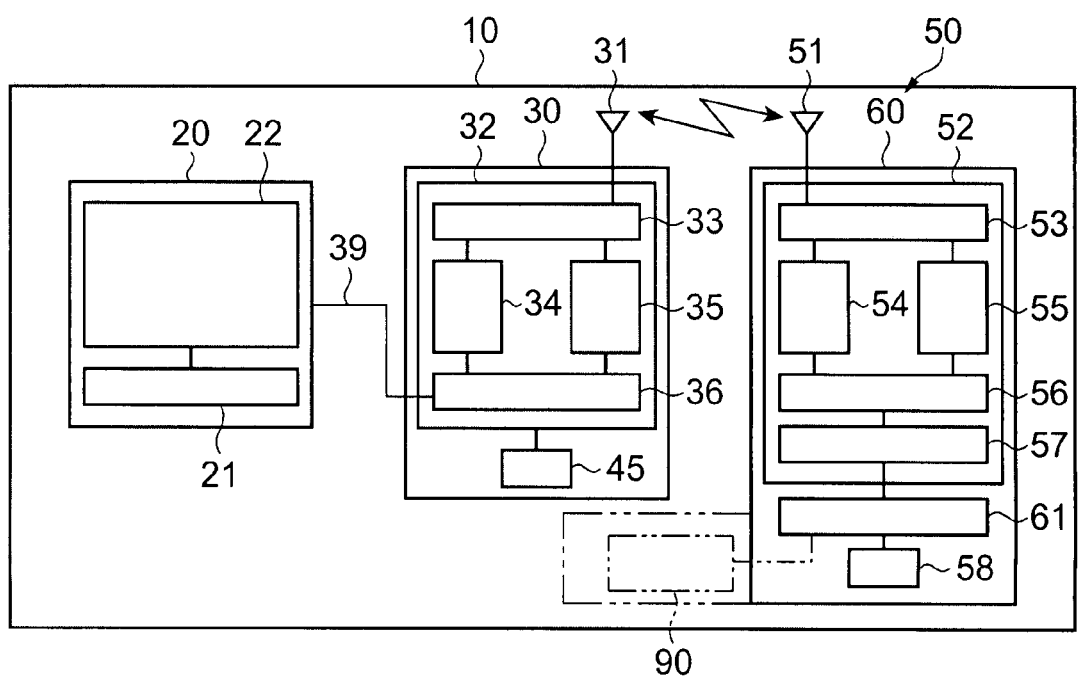
FIG. 1 is a block diagram showing a configuration of a fluid transportation system according to a first embodiment of the invention.
Figure 2:
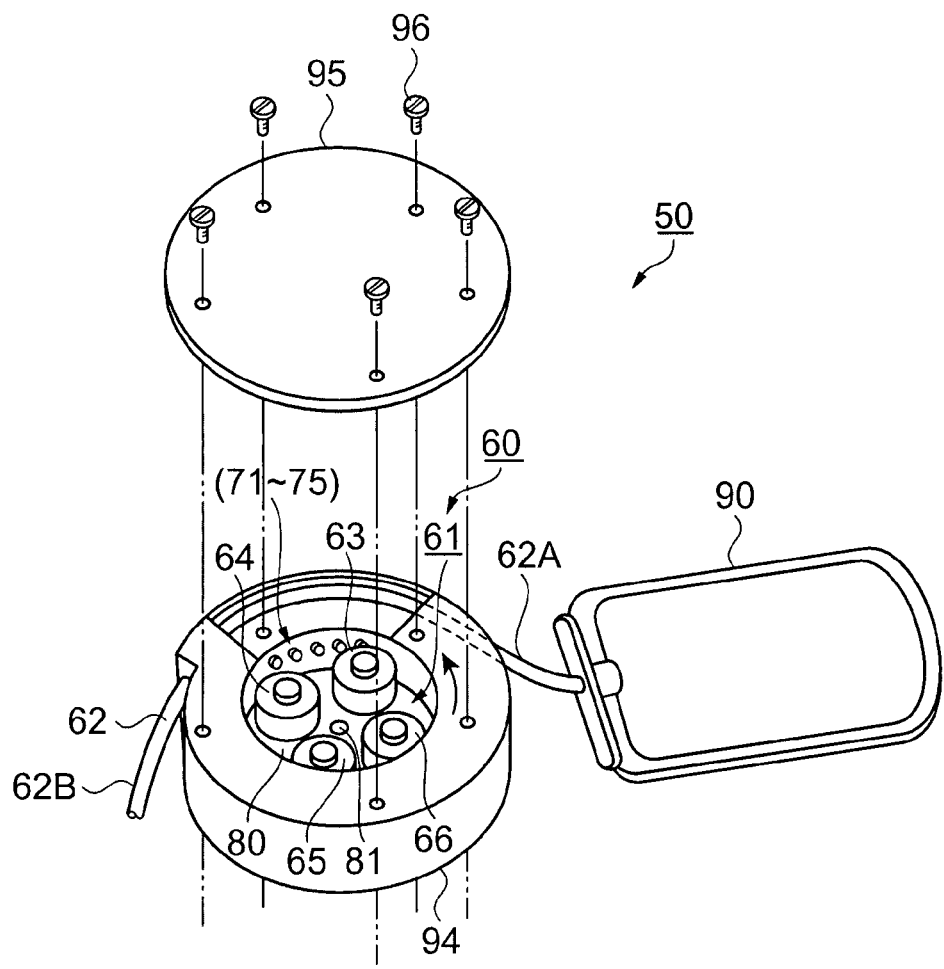
FIG. 2 is an exploded perspective view showing a schematic structure of a fluid transportation device according to the first embodiment of the invention.
Figure 3:
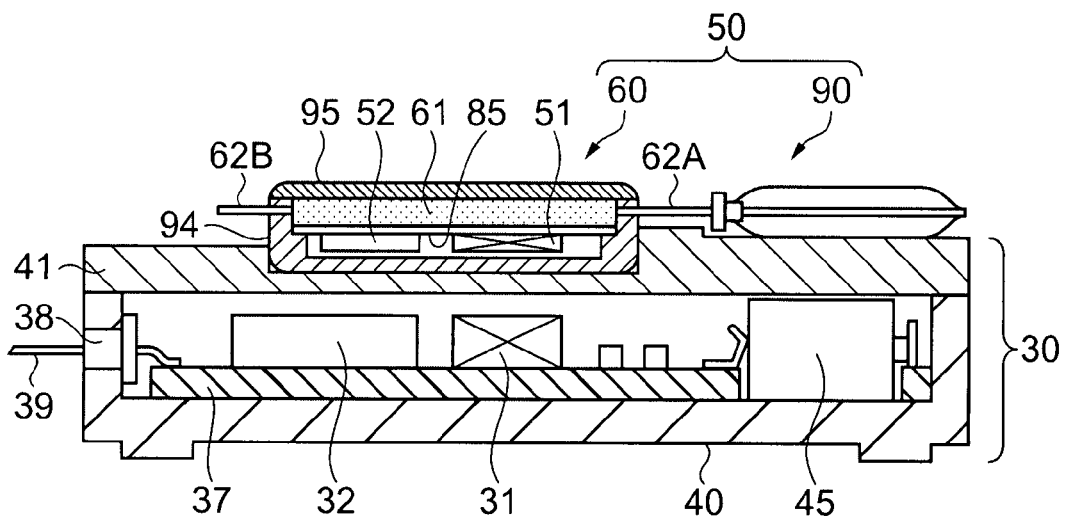
FIG. 3 is a cross-sectional view showing a structure of a communication device and the fluid transportation device according to the first embodiment of the invention.

FIGS. 1 through 3 show a fluid transportation system and a fluid transportation device according to the first embodiment of the invention.

FIG. 1 is a block diagram showing a configuration of the fluid transportation system 10 according to the present embodiment. In FIG. 1, as a fundamental configuration, the fluid transportation system 10 of the present embodiment is composed of a personal computer (PC) 20 as an ejection data processing device, a communication device 30, and a fluid transportation device 50.

The PC 20 includes an operation section 21 as an input device for inputting driving condition data of the fluid transportation device 50, a display section 22 for displaying the driving condition data thus input, and in addition, functions provided to a general PC such as an calculation function, storage function, and so on. The driving condition data input to the PC 20 is transmitted to the communication device 30 via a Universal Serial Bus (USB) cable 39.

The communication device 30 is composed of a communication control circuit 32 for controlling the overall communication device 30, an antenna 31, and a battery 45 as a power supply. The communication control circuit 32 is composed of a memory circuit 36 for storing the driving condition data, a reception control circuit 34, a transmission control circuit 35, and a transmission/reception switcher 33.

The driving condition data stored in the memory circuit 36 is converted into a transmission signal by the transmission control circuit 35, and then transmitted to a micro pump module 60 of the fluid transportation device 50 via the transmission/reception switcher 33 and the antenna 31 by way of radio wave wireless communication. The transmission/reception switcher 33 has a function of switching transmission and reception in the communication device 30.

It should be noted that although the structure of having the battery 45 built-in in the communication device 30 is shown in the drawings as the power supply, a structure of taking in the commercial power supply from the outside can also be adopted. In this case, a power control circuit is implemented. In the case in which the battery 45 is adopted, a battery voltage detection circuit not shown is provided. Further, it is possible to take in the power from the USB cable 39 for connecting the PC 20 and the communication device 30 to each other.

The fluid transportation device 50 is composed of the micro pump module 60, the antenna 51, and a fluid container 90 for containing the fluid. The micro pump module 60 includes a fluid transportation device control circuit 52 for performing overall control of the fluid transportation device 50, a pump unit 61 as means for transporting the fluid, and the battery 58 as a power supply. The fluid transportation device control circuit 52 is composed of a drive control circuit 57 for performing drive control of the pump unit 61, the transmission/reception switcher 53 for accepting the driving condition data input from the antenna 51, a reception control circuit 54 for converting the input signal into the signal for the drive control, a memory circuit 56 for storing the signal thus converted, and a transmission control circuit 55 for converting the ejection information data in the case in which the pump unit 61 is actually driven into a transmission signal and output it to the antenna 51.

The transmission/reception switcher 53, the reception control circuit 54, and the transmission control circuit 55 form a communication section for the fluid transportation device 50.

Further, the transmission control circuit 55 is additionally provided in order for transmitting the driving status data and so on in the case in which the pump unit 61 is driven to the PC 20.

Further, although not shown in the drawings, the drive control circuit 57 is provided with a timer for controlling the driving period.

Then, the operation of the fluid transportation system 10 according to the present embodiment will be explained.

Firstly, the driving condition data for driving the fluid transportation device 50 in a predetermined condition is input to the PC 20 by operating the operation section 21. The operation section 21 is a keyboard.

It should be noted here that, although details will be described later, the driving condition data input thereto includes at least fluid flow per unit time, driving period, drive in the case of intermittent drive, and so on, and in addition, an identification number or code of the fluid transportation device and so on is also conceivable.

The driving condition data thus input thereto is displayed on the display section 22, thus the content thereof can be confirmed.

Subsequently, the driving condition data necessary for the communication device 30 is transmitted by operating the operation section 21. The communication device 30 transmits the driving condition data thus input thereto to the fluid transportation device 50. As the wireless communication, a communication method such as proximity communication or short range communication can be adopted, wherein in the case of the proximity communication, the fluid transportation device 50 is mounted on the communication device 30 (see FIG. 3), while in the case of the short range communication, the arrangement of the communication device 30 and the fluid transportation device 50 is not particularly limited providing they are disposed within a range in which the radio wave can be propagated.

The fluid transportation device 50 is driven in accordance with the driving condition data thus input thereto. On this occasion, an ejection amount (replaced with a rotation number of a roller support 80 (see FIG. 2)) of the fluid, driving period, a total ejection amount, and so on in the case in which the pump unit 61 is driven are transmitted to the PC 20 via the communication device 30. This operation is also performed by operating the operation section 21 to output the transmission command, or alternatively, they can automatically be transmitted to the PC 20 after predetermined driving status data is accumulated in the memory circuit 56.

Further, if it is arranged that the driving condition data input from the PC 20 is once received, and then transmitted to the PC 20, displayed on the display section 22 to confirm whether or not the driving condition data is accurately stored in the fluid transportation device 50, the reliability thereof can further be improved.

In the PC 20, the driving status data thus input is converted into a table or a graph, and displayed on the display section 22. It should be noted that it is further preferable to perform alarm display in the case in which a difference occurs in comparing the driving status data with the driving condition data.

Subsequently, the structure of the fluid transportation device 50 according to the present embodiment will be explained with reference to the drawings.

FIG. 2 is an exploded perspective view showing a schematic structure of the fluid transportation device 50. In FIG. 2, the fluid transportation device 50 is composed of the micropump module 60 and the fluid container 90 as a fundamental configuration.

The micro pump module 60 is provided with a chassis composed of a case section 94 and a lid body 95, and the pump unit 61 and the fluid transportation device control circuit 52 (see FIG. 1) described above, the pump unit 61 and the fluid transportation device control circuit 52 being housed inside the chassis. The pump unit 61 is provided with a stepping motor as a drive source not shown and a gear train for transmitting the drive force from the stepping motor to the roller support 80.

In the periphery of the roller support 80, there are mounted four rollers 63 through 66 at substantially even intervals. In the periphery of the case section 94, there is formed a groove along the roller support 80, and a tube 62 is mounted in the groove.

Through the wall between the groove described above and a recess section housing the roller support 80 provided to the case section 94, there are inserted pressing shafts 71 through 75. The pressing shafts 71 through 75 are disposed radially from the rotational shaft 81 of the roller support 80 and at substantially even intervals from the right-hand side of the drawing, and are arranged to be slidable in the axial directions.

The tube 62 is a narrow tube made of elastic silicone rubber, and extends with an outflow end 62B and a container-connection end 62A protruded from the case section 94. As the tube 62, a material having elasticity and biocompatibility is adopted, and specifically, in the present embodiment silicone rubber is adopted. Polyethylene resin or fluorinated resin can also be adopted besides the silicone rubber, and the material is selected in consideration of chemical resistance and so on corresponding to the type of the fluid used therein.

The container-connection end 62A of the tube 62 is connected to the fluid container 90. The structure in which the tube 62 and the fluid container 90 are detachably attached to each other is adopted, so that the fluid container 90 can be replaced. Alternatively, an integral structure in which the tube 62 and the fluid container 90 are unable to be separated from each other can also be adopted.

The fluid container 90 is a pack-like container made of the same material as that of the tube 62, and formed to have a variable thickness.

Further, the lid body 95 is attached to the case section 94. Although in the present embodiment, the lid body 95 is screwed with four fixing screws 96, welding fixation or adhesive fixation can also be adopted as the fixing structure, and in addition, a structure or adhesive fixation provided with a gasket disposed between the lid body 95 and the case section 94 or between the tube 62 and the end portion of the case section 94 can also be adopted. The inside of the chassis is thus sealed to have a waterproof property, making it possible to be mounted inside a body of a small animal for the purpose of developing a new drag and so on.

It should be noted that the case section 94, the lid body 95, and the fluid container 90 have rounded outer corners, and are arranged to have shapes with no salient, so as to have shapes not causing damages to a living body even if they are mounted inside or outside the living body.

Further, although in the present embodiment, the structure having the micro pump module 60 and the fluid container 90 as separate bodies, a structure having the fluid container inside the chassis can also be adopted.

It should be noted that the fluid housed in the fluid container 90 is not particularly limited providing it is what has fluidity such as water, a salt solution, a medicinal liquid, an oil, an aromatic liquid, ink, or a gas.

Then, driving of the micro pump module 60 will be explained with reference to FIG. 2.

The roller support 80 is rotated in the direction of the arrow shown in the drawing around the rotational shaft 81 by the stepping motor along an instruction of the drive control circuit 57. In accordance with the rotation of the roller support 80, each of the rollers 63 through 66 presses the pressing shafts 71 through 75 sequentially. On this occasion, the pressing shafts 71 through 75 squeeze the tube 62 from the side of the fluid container 90 to transport the fluid, and thus the fluid is ejected from the outflow end 62B of the tube 62.

Such a motion of the pressing shafts is called a peristaltic motion, and a pump using the peristaltic motion is called a peristaltic pump. The peristaltic pump is suitable for a miniature pump capable of continuously transporting a small amount of fluid.

Subsequently, an example of a configuration of the communication device 30 and the fluid transportation device 50 according to the present embodiment will be explained with reference to the drawings. Reference to FIGS. 1 and 2 is also required.

FIG. 3 is a cross-sectional view showing a structure including the communication device 30 and the fluid transportation device 50. FIG. 3 shows an example adopting the wireless proximity communication. In FIG. 3, the fluid transportation device 50 is mounted on the upper surface of the communication device 30.

The communication device 30 is configured including a chassis composed of a case section 40 and a lid body 41, and a circuit board 37, the communication control circuit 32 mounted on a surface of the circuit board 37, the antenna 31, other circuit components not shown, the battery 45 as the power supply, and a USB connector 38 mounted inside the chassis. On the upper surface of the lid body 41 there is formed a recess section in which the micro pump module 60 is mounted.

The micro pump module 60 has the pump unit 61, a circuit board 85, the fluid transportation device control circuit 52, and the antenna 51 housed in a space formed of the case section 94 and the lid body 95, wherein the antenna 51 is disposed at a position substantially opposed to the antenna 31 of the communication device 30. Further, the fluid container 90 is mounted on the upper surface of the communication device 30 while being connected to the micro pump module 60.

In the condition of thus mounting the fluid transportation device 50 on the communication device 30, setting of the driving condition or a startup instruction is performed by operating the operation section 21 of the PC 20, and communication is performed between the antennas 31, 51, thus necessary data is transmitted. In the case in which the short-range wireless communication is adopted as the communication method, it is not necessarily required that the fluid transportation device 50 is mounted on the communication device 30, but it is enough for the devices to locate within a range in which the radio wave can be propagated.

Therefore, according to the first embodiment described above, there can be provided an easy-to-handle fluid transportation system which is composed of the fluid transportation device 50, the PC 20, and the communication device 30, thus the driving condition data for making the fluid transportation device 50 perform a predetermined operation is input from the PC 20, the fluid transportation device 50 is driven in accordance with the driving condition, and consequently setting of the ejection rate (ejection amount) can be performed with a feeling as if handling a general PC.

Further, since the fluid transportation system 10 can display the driving condition data and the driving status data of the fluid transportation device 50 with the display section 22 of the PC 20, it is preferable for controlling the fluid transportation system of a fluid such as a medicinal liquid to which accurate flow rate control is required.

Further, since the fluid transportation device 50 and the PC 20 are connected by the communication device 30, it is enough for the fluid transportation device 50 to implement only the functions directly related to the fluid transportation, thus the fluid transportation device can be downsized.

Further, by adopting the configuration described above, the fluid transportation device 50 and the PC 20 can be configured separately from each other, thus the outer shape of the fluid transportation device 50 can be simplified and shrunk. Still further, since the wireless communication section is provided, the communication is possible even if a partition wall lies between the fluid transportation device 50 and the PC 20, thus the limitation in usage environment regarding the communication can be eased. Assuming that the fluid transportation device 50 is mounted inside a living body, the communication becomes possible in the condition of mounting the fluid transportation device 50 inside the living body.

Further, since there is no salient on the chassis of the fluid transportation device 50 or the outer shape of the fluid container 90, and the case section 94, the lid body 95, and the tube 62 are made of a material having biocompatibility, the fluid transportation device 50 can be mounted inside or outside the living body, and further, since it is made of a material having a good compatibility with the living body, development of rejection, allergic symptoms, and so on can be alleviated.

The micro pump module 60 houses the fluid transportation device control circuit 52 including the pump unit 61 as described above, and consequently, is sensitive to moisture, dust, or the like. Therefore, by adopting a structure for sealing the inside of the micro pump module 60, infiltration of moisture, dust, and so on can be prevented, thus there can be obtained an advantage that the fluid transportation with a high reliability can be continued even when the fluid transportation device 50 is mounted inside a living body.

Hereinafter, a fluid transportation system according to a second embodiment of the invention will be explained with reference to FIGS. 4 and 5. The second embodiment has a feature with respect to the first embodiment in that optical communication is adopted as the communication method. Therefore, the explanation is focused on the configuration and structure relating to the optical communication. The explanation of the intersection with the first embodiment will be omitted, and the same reference numerals are used in the explanation.

Figure 4:
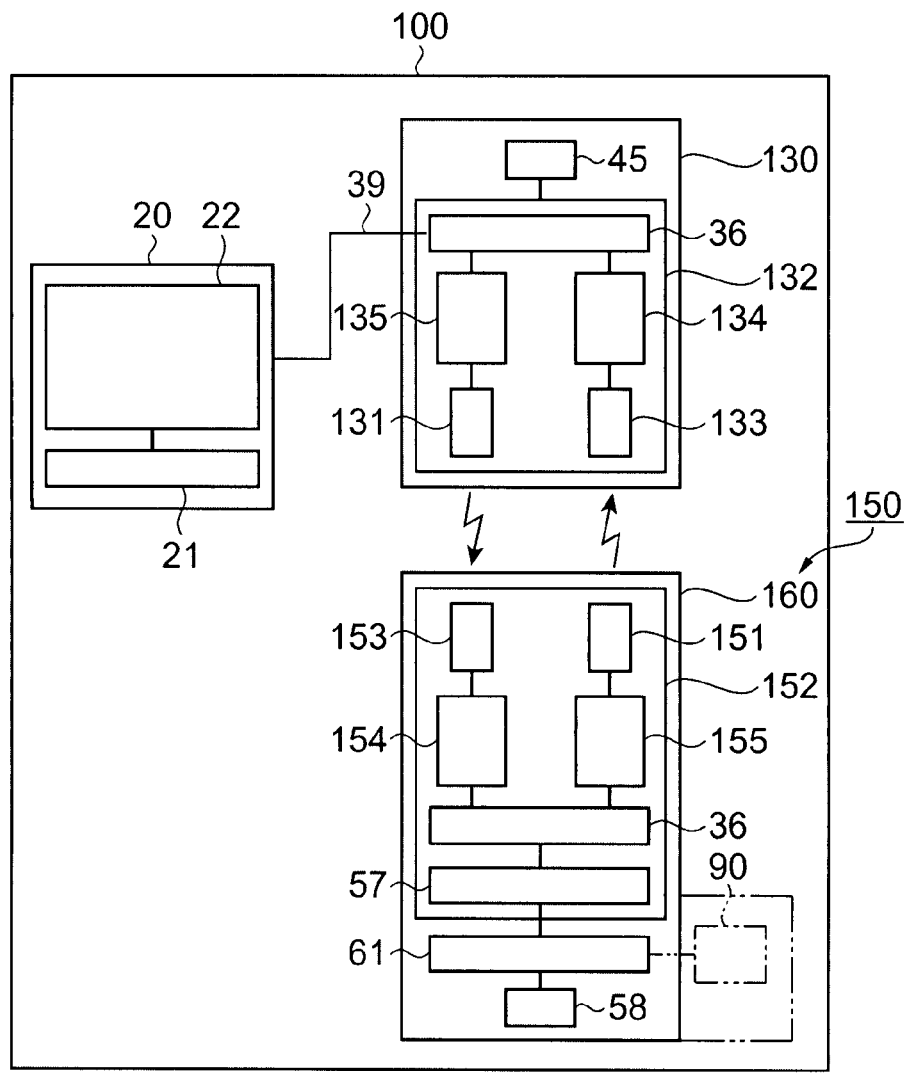
FIG. 4 is a block diagram showing a configuration of a fluid transportation system according to a second embodiment of the invention.

FIG. 4 is a block diagram showing the configuration of the fluid transportation system 100 according to the second embodiment. In FIG. 4, the fluid transportation system 100 is composed of the PC 20 as the ejection data processing device, a communication device 130, and a fluid transportation device 150.

The communication device 130 is composed of a communication control circuit 132, and the battery 45 as the power supply, and the communication control circuit 132 is composed of the memory circuit 36, a light reception control circuit 134, a light emission control circuit 135, a light receiving element 133, and a light emitting element 131. The driving condition data is input to the fluid transportation device 150 by means of an optical signal emitted from the light emitting element 131.

The fluid transportation device 150 is composed of a micro pump 160 including a fluid transportation device control circuit 152 and the pump unit 61, the battery 58 as the power supply, and the fluid container 90, and the fluid transportation device control circuit 152 is composed of a communication section formed of a light emitting element 151, a light receiving element 153, a light emission control circuit 155, and a light reception control circuit 154, the memory circuit 56, and the drive control circuit 57.

It should be noted that the same frequency band in the infrared area is used for both of the light emitting elements 131, 151.

Then, the operation of the fluid transportation system according to the present embodiment will be explained.

Firstly, the driving condition data for driving the fluid transportation device 150 in a predetermined condition is input to the PC 20 by operating the operation section 21.

Here, the driving condition data input therein is the same as that of the first embodiment described above. The driving condition data thus input thereto is displayed on the display section 22, thus the content thereof can be confirmed.

Subsequently, the driving condition data required therefor is transmitted to the communication device 130 by operating the operation section 21. The communication device 130 transmits the driving condition data thus input thereto to the fluid transportation device 150. In the present embodiment, the optical communication is adopted as the communication method, and in the optical communication, the arrangement of the communication device 130 and the fluid transportation device 150 has freedom in a range of not blocking the emitted light. However, since the light emitting element 131 and the light receiving element 133 or the light emitting element 151 and the light receiving element 153 are in positions adjacent to each other as shown in FIG. 5, it is preferable to dispose the elements so that the communication is performed without an influence of an external optical noise.

The fluid transportation device 150 is driven in accordance with the driving condition data thus input thereto. Further, the fluid transportation system 100 is capable of performing both transmission and reception, and consequently, it can transmit the status of the pump unit 61 thus driven to the PC 20 via the communication device 130. Since the transmission of the driving status data to the communication device 130 is also the same as in the first embodiment except using the optical communication, the explanations therefor will be omitted.

Subsequently, an example of a configuration of the communication device 130 and the fluid transportation device 150 according to the present embodiment in the communication operation will be explained with reference to the drawings. The explanation will be presented with reference also to FIG. 4.

Figure 5:
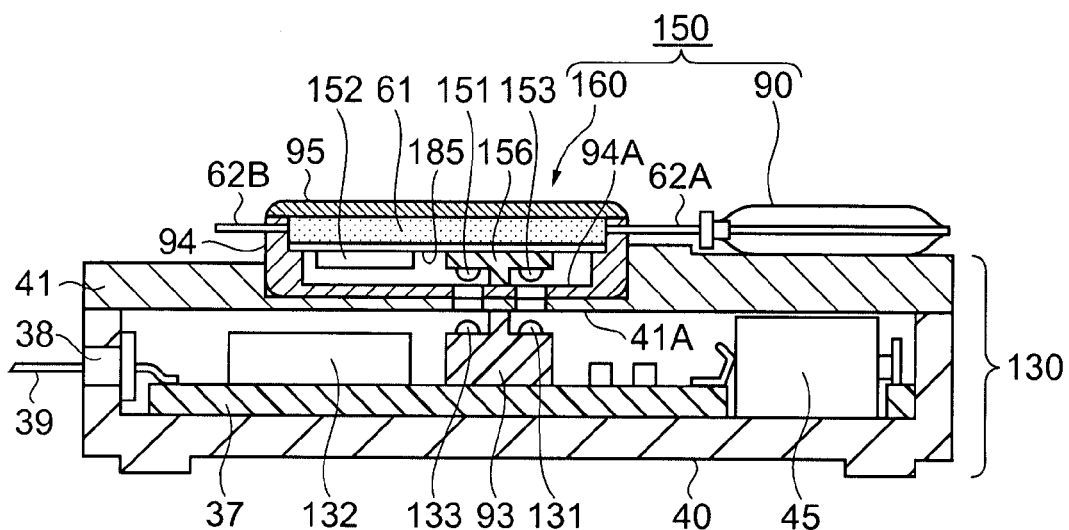
FIG. 5 is a cross-sectional view showing a structure of a communication device and a fluid transportation device according to the second embodiment of the invention.

FIG. 5 is a cross-sectional view showing a structure including the communication device 130 and the fluid transportation device 150. In FIG. 5, the fluid transportation device 150 is mounted on the upper surface of the communication device 130.

The communication device 130 is configured including a chassis composed of a case section 40 and a lid body 41, and a circuit board 37, the communication control circuit 132 mounted on a surface of the circuit board 37, the light emitting element 131, the light receiving element 133, other circuit components not shown, the battery 45 as the power supply, and the USB connector 38 mounted inside the chassis. On the upper surface of the lid body 41 there is formed the recess section in which the micro pump 160 is mounted.

The micro pump 160 has the pump unit 61, a circuit board 185, the fluid transportation device control circuit 152 mounted on the circuit board 185, the light emitting element 151, the light receiving element 153, and the battery 58 housed in the space formed of the case section 94 and the lid body 95, and the light receiving element 153 is disposed at the position substantially opposed to the light emitting element 131 of the communication device 130. Further, the light emitting element 151 is disposed at the position opposed to the light receiving element 133 of the communication device 130.

The light emitting element 151 and the light receiving element 153 are mounted on an element support 156, and respectively connected to the light emission control circuit 155 and the light reception control circuit 154 via lead wires not shown. Further, the light emitting element 131 and the light receiving element 133 are mounted on an element support 93, and respectively connected to the light emission control circuit 135 and the light reception control circuit 134 via lead wires not shown.

In the positions where the light emitting element 151 and the light receiving element 153, and the light receiving element 133 and the light emitting element 131 are respectively opposed to each other, the bottom 41A of the lid body 41 of the communication device 130 and the bottom 94A of the case section 94 of the micro pump 160 are each provided with a light transmissive window.

The fluid container 90 is mounted on the upper surface of the communication device 130 while being connected to the micro pump 160.

In the condition in which the fluid transportation device 150 is thus mounted on the communication device 130, the operation section 21 of the PC 20 is operated to perform communication.

Therefore, according to the second embodiment described above, although the optical communication section has an additional limitation in the communication environment that the communication is inhibited by a light blocking matter between the communication device 130 and the fluid transportation device 150 in comparison with the wireless communication method with the radio wave, the optical communication section has a simple configuration and is used for general remote control systems, and consequently, reduction in cost can be expected.

Subsequently, a third embodiment of the invention will be explained with reference to FIGS. 6, 7, and 8. The third embodiment has a feature in wired communication, namely that connection terminals are provided between the communication device and the fluid transportation device in comparison with that the first and second embodiments respectively adopt wireless communication and optical communication as the communication method. Therefore, the explanation will be focused on a peripheral structure and configuration of the connection terminals, the explanation regarding the intersection with the first or the second embodiment will be omitted, and the same reference numerals are used therefor in the explanation.

Figure 6:
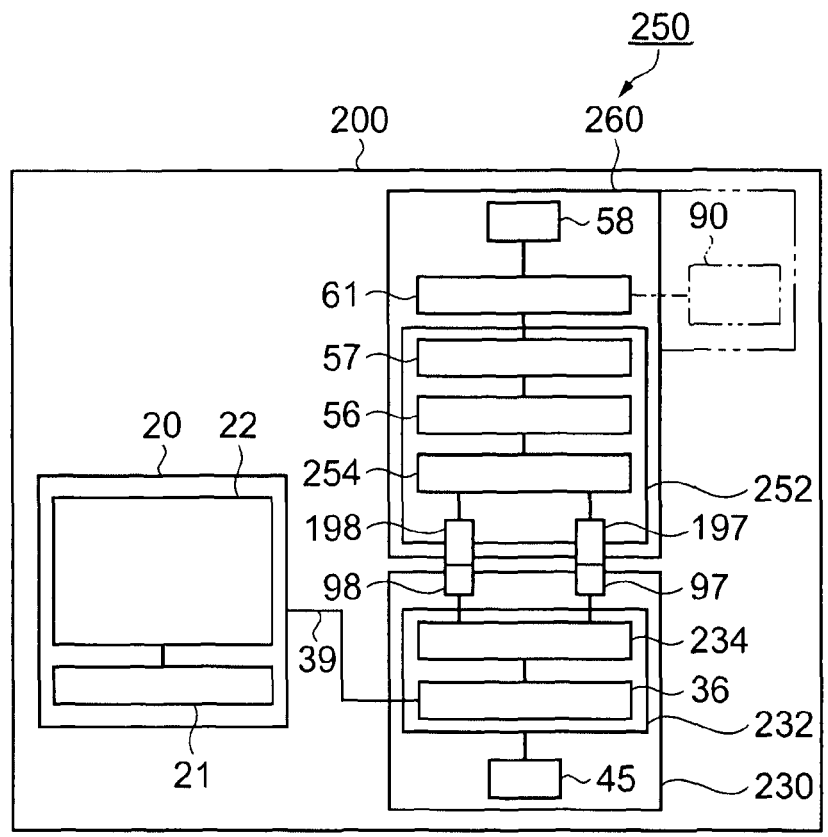
FIG. 6 is a block diagram showing a configuration of a fluid transportation system according to a third embodiment of the invention.

FIG. 6 is a block diagram showing the configuration of a fluid transportation system 200 according to the third embodiment. In FIG. 6, the fluid transportation system 200 is composed of the PC 20 as the ejection data processing device, a communication device 230, and a fluid transportation device 250.

The communication device 230 is composed of a communication control circuit 232 including the memory circuit 36 and transmission reception control circuit 234, and the battery 45 as the power supply. Further, connection terminals 97, 98 as second connection terminals are connected to the transmission reception control circuit 234. The communication is established by the connection terminals 97, 98 having contact with connection terminals 197, 198 as first connection terminals provided to a micro pump module 260.

The fluid transportation device 250 is composed of the micro pump module 260 including the pump unit 61 and a fluid transportation device control circuit 252, the battery 58 as the power supply, and the fluid container 90, and the fluid transportation device control circuit 252 is composed of the drive control circuit 57, the memory circuit 56, and the transmission reception control circuit 254. The transmission reception control circuit 254 and the connection terminals 197, 198 form a communication section in the fluid transportation device 250.

Then, the operation of the fluid transportation system 200 according to the present embodiment will be explained.

Firstly, the driving condition data for driving the fluid transportation device 250 in a predetermined condition is input to the PC 20 by operating the operation section 21.

Here, the driving condition data input therein is the same as in the first and second embodiments described above. The driving condition data thus input thereto is displayed on the display section 22, thus the content thereof can be confirmed.

Subsequently, the driving condition data required therefor is transmitted to the communication device 230 by operating the operation section 21. The communication device 230 transmits the driving condition data thus input thereto to the fluid transportation device 250. In the present embodiment, the wired communication by the connection terminals is adopted as the communication section, and the communication is established by the connection terminals 97 and 98 respectively having contact with the connection terminals 197 and 198 (see FIG. 7).

The fluid transportation device 250 is driven in accordance with the driving condition data thus input thereto. On this occasion, the status obtained as a result of driving the pump unit 61 or the status of presently driving the pump unit 61 is transmitted to the PC 20 via the communication device 230. Since the content of the driving status data and the method of transmission of the driving status data to the communication device 230 are also the same as in the first and second embodiments except adopting the wired communication, the explanations thereof will be omitted.

Subsequently, a condition in which the communication device 230 and the fluid transportation device 250 according to the present embodiment are connected to each other will be explained with reference to the drawings. The explanation will be presented with reference also to FIG. 6.

Figure 7:
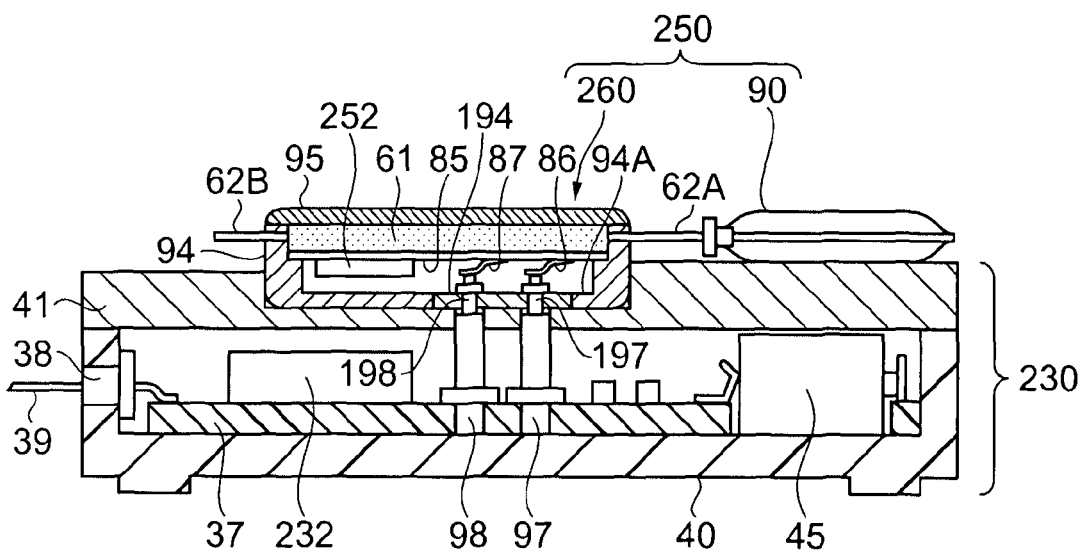
FIG. 7 is a cross-sectional view showing a schematic structure of a communication device and a fluid transportation device in a mounted condition according to the third embodiment of the invention.

FIG. 7 is a cross-sectional view showing a schematic structure in the case in which the communication device 230 and the fluid transportation device 250 are attached to each other. In FIG. 7, the fluid transportation device 250 is mounted on the upper surface of the communication device 230.

The micro pump module 260 is mounted inside a recess section provided to the lid body 41 of the communication device 230. On this occasion, the sizes of the micro pump module 260 and the recess section are arranged so that each of them can be positioned accurately.

The communication device 230 is configured including the chassis composed of the case section 40 and the lid body 41, and the circuit board 37, the communication control circuit 232 mounted on the surface of the circuit board 37, other circuit components, the battery 45 as the power supply, and the USB connector 38 mounted inside the chassis. On the upper surface of the lid body 41 there is formed the recess section in which the micro pump module 260 is mounted.

Figure 8A:
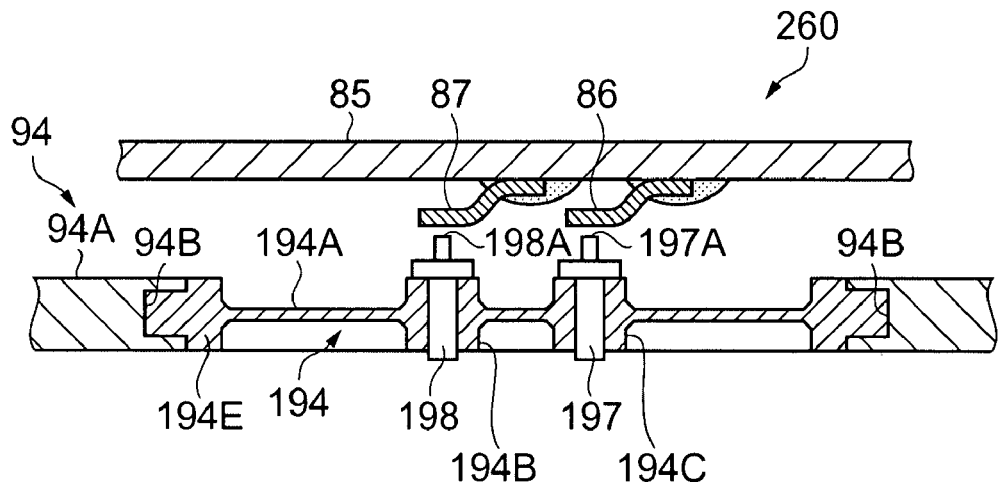
FIG. 8A is a partial cross-sectional view showing the structure of a pump around a connection terminals thereof according to the third embodiment of the invention.
Figure 8B:
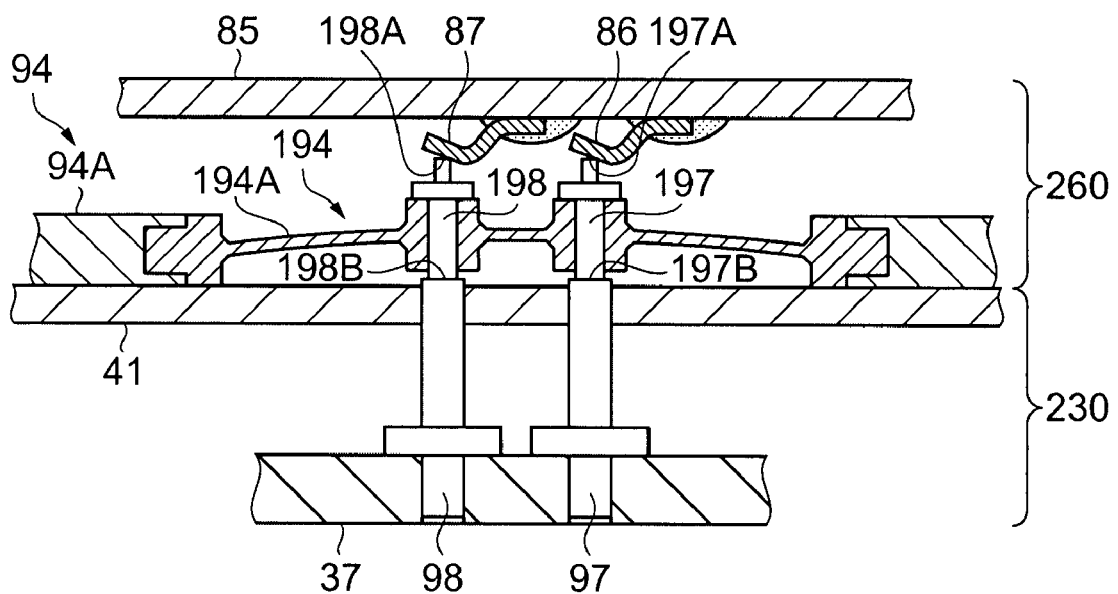
FIG. 8B is a partial cross-sectional view showing a connection structure between a communication device and the pump.

The circuit board 37 is provided with two connection terminals 97, 98 implanted to stand thereon, and the tip portions of the connection terminals project on the side of the micro pump module 260 penetrating the lid body 41 (see FIGS. 8A and 8B for details). The connection terminals 97, 98 are each connected to the transmission reception control circuit 234 with a wiring pattern provided to the circuit board 37.

The micro pump module 260 has the circuit board 85, the fluid transportation device control circuit 252 mounted on the surface of the circuit board 85, the pump unit 61, and the battery 58 not shown housed inside the chassis formed of the case section 94 and the lid body 95. The circuit board 85 is provided with connection springs 86, 87, and the connection springs 86, 87 are each connected to the transmission reception control circuit 254 (see FIG. 6) with a wiring pattern provided to the circuit board 85.

The bottom 94A of the case section 94 of the micro pump module 260 is provided with a seal member 194 attached thereto, and the connection terminals 197, 198 are implanted penetrating the seal member 194. The connection terminals 197, 198 are disposed at positions respectively opposed to the connection terminals 97, 98 provided to the communication device 230. The structure of the connection terminals and the periphery thereof will be explained in further detail with reference to FIGS. 8A and 8B.

FIGS. 8A and 8B show the structure relating to the connection between the communication device 230 and the micro pump module 260 according to the third embodiment, wherein FIG. 8A shows the structure of the periphery of the connection terminals of the micro pump module 260, and FIG. 8B shows the structure of the communication device 230 and the micro pump module 260 connected to each other.

FIG. 8A is a partial cross-sectional view showing the structure relating to the connection terminals 197, 198 provided to the micro pump module 260. In FIG. 8A, the bottom 94A of the case section 94 is provided with the seal member 194 attached thereto.

The bottom 94A of the case section 94 is provided with a circular opening section, the inner peripheral surface of the opening section is provided with a groove 94B having a substantially bracket cross-section, and the outer periphery of the seal member 194 is inserted into the groove 94B so as to adhere thereto. The seal member 194 is made of a material having elasticity and biocompatibility, and specifically, in the present embodiment silicone rubber is adopted.

The seal member 194 has a disk like shape, and is composed of a peripheral section 194E, an elastic section 194A, and connection terminal fixing sections 194B, 194C. At the center sections of the connection terminal fixing sections 194B, 194C, there are press-fitted and fixed the connection terminals 198, 197. The peripheral section 194E and the connection terminal fixing sections 194B, 194C are portions formed with a larger thickness, wherein the peripheral section 194E has a necessary thickness for assuring the fixing strength with the case section 94, and the connection terminal fixing sections 194B, 194C have a necessary thickness for assuring the fixing strength and adhesiveness with the connection terminals 198, 197, respectively.

Further, the elastic section 194A formed to have a thickness easy to bend when connecting the communication device 230 described later and the micro pump module 260 to each other. Further, FIG. 8A shows the state in which the micro pump module 260 is not connected to the communication device 230, and in this state, the connection terminal tip portions 197A, 198A are not connected to the connection terminal springs 86, 87, respectively.

It should be noted that as a material of the connection terminals 197, 198, the material having biocompatibility and electrical conductivity is selected, and in the present embodiment, titanium or a titanium alloy is adopted.

Subsequently, the state in which the micro pump module 260 is mounted on the communication device 230 will be explained with reference to the drawings.

FIG. 8B is a partial cross-sectional view showing the state in which the micro pump module 260 is mounted on the communication device 230. In FIG. 8B, in the state in which the micro pump module 260 is mounted on the communication device 230, the connection terminals 97, 98 implanted to stand on the circuit board 37 of the communication device 230 respectively push up the lower ends 197B, 198B of the connection terminals 197, 198 implanted to stand on the seal member 194 of the micro pump module 260.

When the connection terminals 197, 198 are pushed up, the elastic section 194A of the seal member 194 is distorted, and the connection terminal tip portions 197A, 198A respectively press the connection terminal springs 86, 87. By this operation, the communication device 230 and the micro pump module 260 are connected to each other, thus enabling the communication.

When the micro pump module 260 is detached from the communication device 230, the state shown in FIG. 8A is restored by the elastic force of the elastic section 194A to establish the state where the communication is disabled, and in addition, the driving condition data can also be prevented from being broken by an external noise.

Therefore, according to the third embodiment described above, since the fluid transportation device 250 and the communication device 230 are respectively provided with the connection terminals 197, 198 and the connection terminals 97, 98, and the respective connection terminals are connected to enable the communication by mounting the fluid transportation device 250 (the micro pump module 260) on the communication device 230, reliability of the communication can be improved with the simple structure.

Further, in comparison with the wireless communication section of the first embodiment and the optical communication section of the second embodiment described above, the antenna, the light receiving element, the light emitting element, the control circuit provided accordingly, and so on can be eliminated, thus cost reduction and downsizing can be achieved.

Further, the connection between the fluid transportation device 250 and the communication device 230 is broken by detaching the fluid transportation device 250 from the communication device 230, and the fluid transportation device 250 can be driven by itself, and consequently, an advantage of being hardly influenced by an external noise can also be obtained.

Subsequently, a fourth embodiment of the invention will be explained with reference to the drawings. The fourth embodiment has a feature of making the structure of the third embodiment described above simpler.

Figure 9:
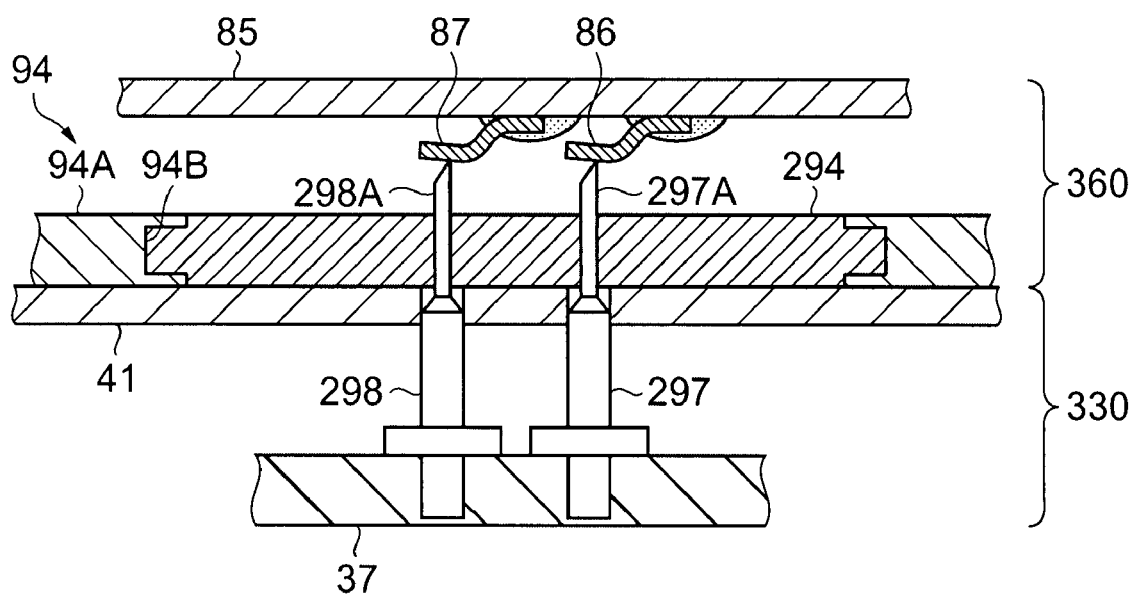
FIG. 9 is a partial cross-sectional view showing a condition in which a pump according to a fourth embodiment of the invention is mounted on a communication device.

FIG. 9 is a partial cross-sectional view showing the state in which a micro pump module 360 according to the fourth embodiment is mounted on a communication device 330. In FIG. 9, connection terminals 297, 298 are implanted to stand on the circuit board 37 of the communication device 330.

On the tips of the connection terminals 297, 298, there are formed needle sections 297A, 298A with keen tips, respectively. The needle sections 297A, 298A penetrate the lid body 41.

Further, a seal member 294 is attached to the bottom 94A of the case section 94 of the micro pump module 360. Since the mounting structure of the seal member 294 to the bottom 94A is the same as that of the third embodiment, the explanation thereof will be omitted, but the seal member 294 has a simple disc-like shape. The seal member 294 is also made of silicone rubber.

Here, as shown in FIG. 9, when the micro pump module 360 is mounted on the communication device 330, the needle sections 297A, 298A of the connection terminals 297, 298 pierce the seal member 294 to penetrate it. The penetrating needle sections 297A, 298A respectively have contact with the connection terminal springs 86, 87 to connect the communication device 330 and the micro pump module 360 to each other, thus enabling the communication.

Further, when the micro pump module 360 is detached from the communication device 330, the needle sections 297A, 298A come off from the seal member 294. Then, the holes made by piercing the seal member 294 are closed by the elastic force of the seal member itself, and the seal is completed.

Therefore, according to the fourth embodiment described above, when the micro pump module 360 is mounted on the communication device 330, the needle sections 297A, 298A of the connection terminals 297, 298 pierce and penetrate the seal member 294, and when detached, the seal member 294 is closed by the elastic force of the seal member itself, thus the fluid transportation device with a further simpler structure can be achieved.

Subsequently, a method of inputting fundamental data and ejection data to the PC 20 (an ejection data processing device) and a method of setting the ejection amount of a fluid in the fluid transportation system 10 of the embodiment of the invention will be explained with reference to the drawings. It should be noted that the method of setting the ejection amount of a fluid explained herein is compliant to a common specification of the fluid transportation systems explained in the first through fourth embodiment described above.

Firstly, a fundamental data setting method executed by the manufacturer will be explained.

Figure 10:
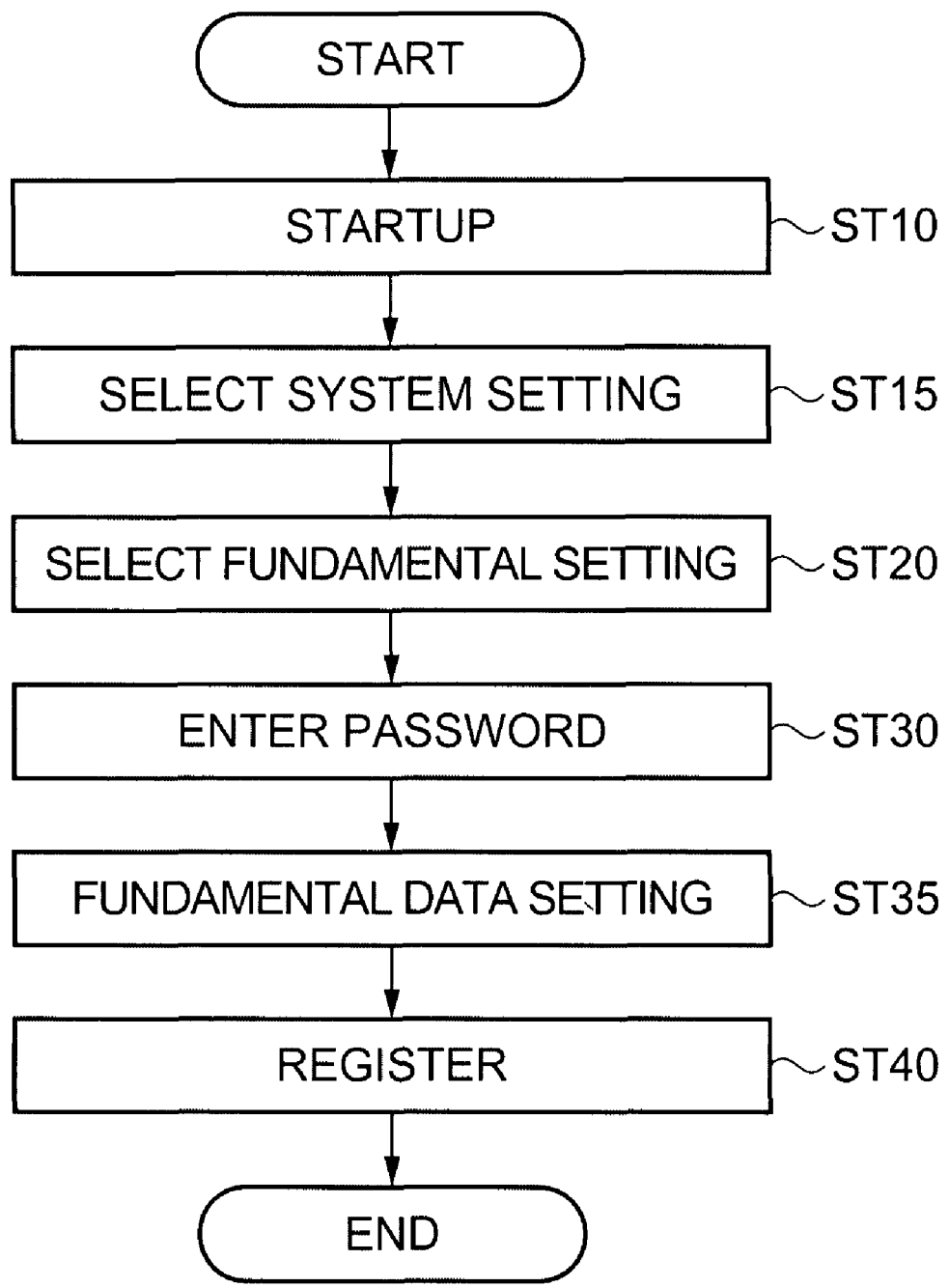
FIG. 10 is an explanatory diagram showing flow of fundamental data setting in an ejection data processing device according to one embodiment of the invention.

FIG. 10 is an explanatory diagram (a flow chart) showing flow of the fundamental data setting executed by the manufacturer. The explanation will be presented with reference to screens displayed on the display section 22 of the PC 20 in accordance with the setting operation. It should be noted that the display screens will be shown in FIGS. 12 through 17. It should also be noted that the display screens are also operation screens when setting the fundamental data or the ejection data.

Firstly, as an initial setting operation, a model name and individual identification number of a manufactured micro pump module 60, a correction coefficient value obtained from the diameter of the corresponding micro pump module 60 and the reference diameter, and so on are displayed on an identification sticker or the like, and the sticker is adhered to the micro pump module 60 at a visible position.

Further, software for the ejection data processing device is previously installed in the PC 20. The software for the ejection data processing device is stored in a storage medium such as a CD-ROM.

Figure 12:
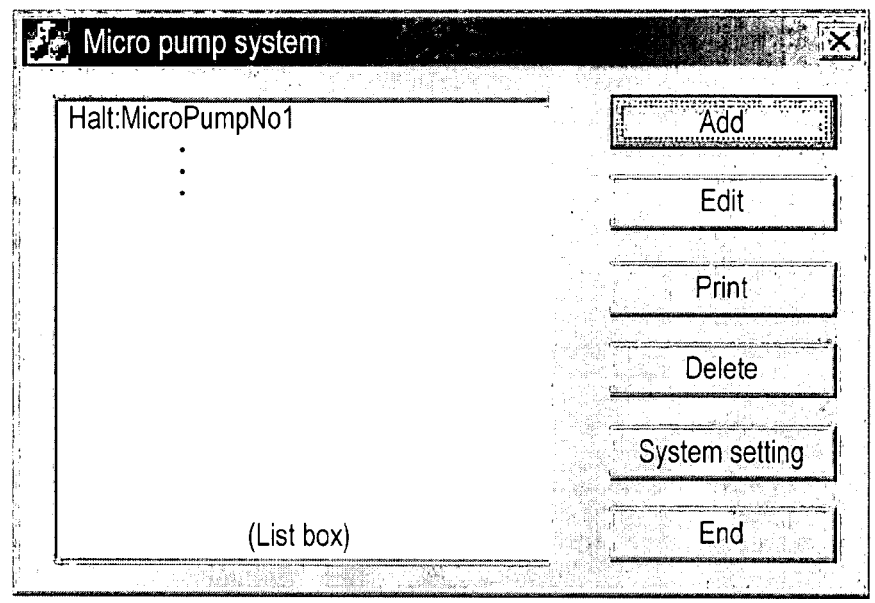
FIG. 12 is an explanatory diagram showing "startup screen" according to one embodiment of the invention.

In FIG. 10, the software is started (ST10) by operating the operation section (a keyboard) 21 of the PC 20. When the software is started, a "Micro pump system" screen as a startup screen shown in FIG. 12 is displayed on the display section 22. There is a list box in the left-hand area of the startup screen, and nothing is displayed thereon when the fundamental data is input (registered) first. If there has been something registered, the list thereof and the respective driving statuses are displayed.

As function indicators (hereinafter abbreviated as buttons) displayed in the "startup screen" shown in FIG. 12, Add, Edit, Print, Delete, System setting, and Exit are provided.

"Add" button is selected in the case in which a name of the micro pump module is newly and additionally registered, and "Edit" button is for selecting a name of the micro pump module already registered and displayed in the list box, and the contents (hereinafter referred to as parameters) of the setting of the registered micro pump module can be edited.

Further, "Print" button has a function for outputting the parameters of the registered micro pump module, by clicking this button after selecting desired one of the micro pump module names in the list box, the parameters of the registered micro pump module is printed-out. On this occasion, a printer not shown is connected to the PC 20.

"Delete" button is used when deleting the registered micro pump module, and by selecting a micro pump module name in the list box, and then clicking the "Delete" button, the micro pump module name and the corresponding parameters are deleted.

"System setting" button is selected when the fluid transportation device 50 is first started, and used for setting a password necessary to be used in the software for the ejection data processing device and a communication port, and further, for proceeding to the step of inputting the first fundamental data.

"Exit" button is clicked when the software for the ejection data processing device is terminated.

Figure 13:
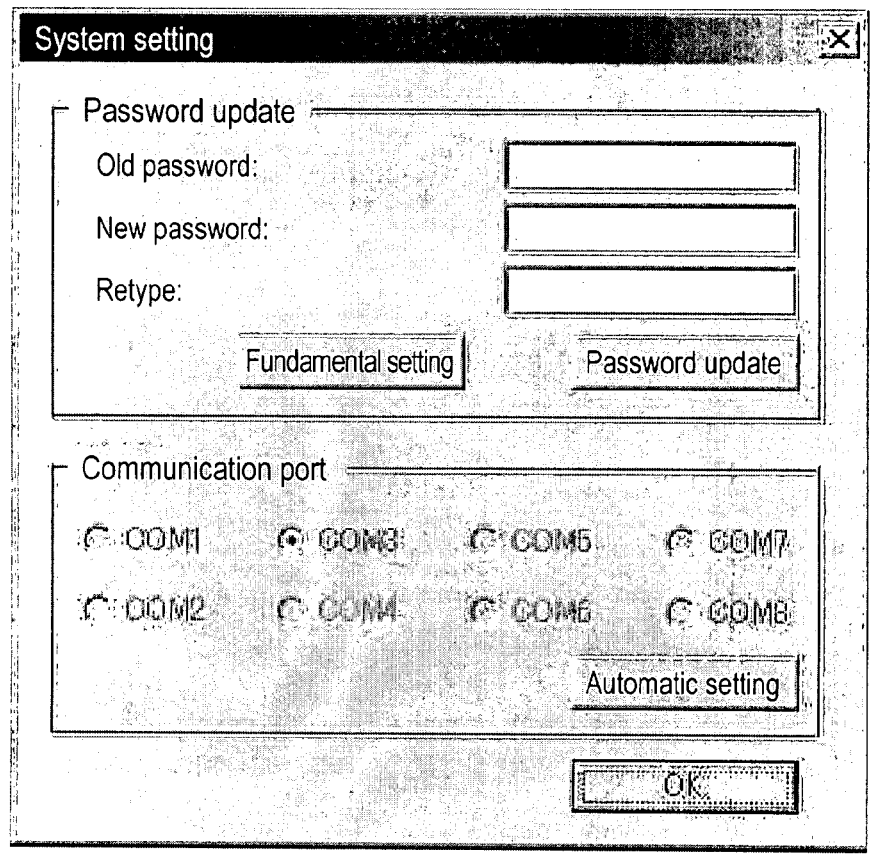
FIG. 13 is an explanatory diagram showing "system setup screen" according to one embodiment of the invention.

Subsequently, a method of proceeding to the next step will be explained. When the software for the ejection data processing device is started for the first time, selection of the system setting is performed in order for inputting the fundamental data (ST15). When the "System setting" button is clicked, a "System setting" screen shown in FIG. 13 is displayed.

In this step, setting or update of the password is performed. For details, when updating the password, after filling in all the boxes of "Old password," "New password," and "Retype new password," "Update password" button should be clicked. When newly registering the password, the password can be input by a similar operation.

Further, when setting the "Communication port," by clicking the "Automatic setting" button, the validated communication port is automatically detected and displayed. It is also possible to manually select a desired communication port.

When proceeding to the fundamental data inputting step, a fundamental setting selection operation (ST20) is performed after the input of the password and so on has been completed. When the "Fundamental setting" button in the "System setting" screen shown in FIG. 13 is clicked, the "Password" screen shown in FIG. 15 is displayed.

It should be noted that other function indicators than the "fundamental setting" relate to functions selected by the user, and consequently, explanation therefor will be presented in the section of user operations described later, and are therefore omitted here.

Figure 15:
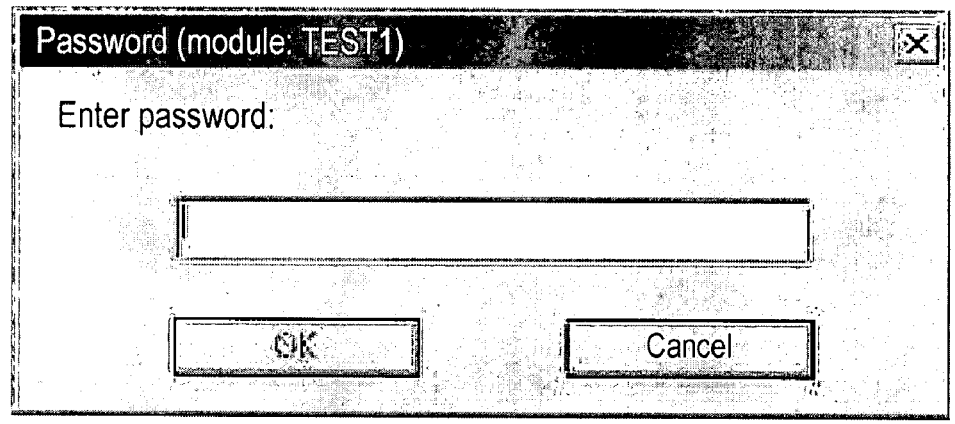
FIG. 15 is an explanatory diagram showing "password setup screen" according to one embodiment of the invention.

FIG. 15 shows the "Password" setting screen. On this occasion, a previously determined password should be input (ST30). When the "OK" button is clicked, a "Fundamental data setting" screen shown in FIG. 16 is displayed.

FIG. 16 shows the "Fundamental data setting" screen. On this occasion, the fundamental data for driving the fluid transportation device should be set in the blank boxes corresponding to the function indicators described in the display screen (ST35). The pull-down menus in the display screen each show that the fundamental data for the item is previously determined stepwise and should be selected among them, while in the other blank boxes arbitrary numerals should be input.

Firstly, the stepping motor drive pulse frequency [Hz] should be selected, and the reference value of the micro pump ejection amount [μl/revolution] should be input. It should be noted that since the correction coefficient is set by the user for individual drive target fluid transportation device, the details thereof will be described later. The correction coefficient of 1000 means that the diameter of the tube is equal to the reference value, the larger value of the correction coefficient shows that the diameter of the tube is greater than the reference value, while the smaller value thereof shows that the diameter of the tube is smaller than the reference value.

How to obtain the correction coefficient according to the present embodiment will be described below. Assuming that the diameter (the reference value) as the design value of the fluid flowing section of the tube 62 is D, and the measured value of the diameter of the tube as the drive target is d, the correction coefficient R is obtained by the following formula. $R=(d/D)^2 \times 1000$ If d=D, then R=1000.

"Micro pump ejection amount [μl/revolution]" is calculated from the product of the reference value of the micro pump ejection amount described above and the correction coefficient, and displayed. Further, the upper limit of the maximum ejection rate [μl/H] is set in the case in which it is necessary for the manufacturer side to put restrictions considering the maximum allowable current of the battery used therein.

Further, an initial ejection rate [μl/H] and an initial driving period [second (S)] are set as the fundamental data of the driving condition in the initial driving term. "Stepping motor pulse width [mS]" is set in accordance with the drive characteristic of the stepping motor.

Stepping motor speed reduction ratio denotes the reduction ratio of the gear train, and is an element for calculating the rotational speed of the roller support with respect to the drive frequency, namely the rotational speed of the stepping motor. "Battery capacity," "Safety ratio," "Stepping motor current consumption [μA/step]," and "CPU in-operation current consumption [μA]," are items forming a basis for setting the driving periods. Therefore, the pump unit 61 has a structure of changing the arrangement of the gear train from the stepping motor to the roller support 80, thereby changing the reduction ratio.

The safely ratio is set by assuming the variation in remaining power with respect to the reference battery capacity [mAH]. Further, a part of the CPU (the fluid transportation device control circuit 52) is in-operation even before the fluid transportation device starts driving, and the current consumption on this occasion is input as the CPU in-operation current consumption.

In the first through the fourth embodiments, a power supply voltage detection circuit is built-in in the drive control circuit 57 to detect the voltage of the battery 58 as the power supply. Firstly, when switching ON/OFF of the "power supply detection circuit" to select ON, "Detection interval of the power supply voltage detection circuit [minute (min)]" is selected from the set values, and "Detection voltage of the power supply voltage detection circuit [V]" is selected from the set values. In FIG. 16, 1.13V is exemplified as the detection voltage. The detection voltage is a threshold voltage for stopping the micro pump module 60, and in this case, if the battery voltage has dropped to lower than 1.13V, the micro pump module 60 is stopped.

After the fundamental data described above has been input to the PC 20, when the "Registration" button is clicked, the fundamental data is written to the software for ejection data processing device (ST40). Therefore, the fundamental data should be written in the CD-ROM where the software for the ejection data processing device is written, and the CD-ROM will be passed together with the fluid transportation device 50 corresponding to the fundamental data written therein.

Further, it is possible to pass the PC 20 itself having the software for the ejection data processing device and the fundamental data written therein to the user.

It should be noted that although on this occasion, the fluid container 90 is passed to the user while being mounted on the micro pump module 60, and the user injects the fluid such as a medicinal liquid in the fluid container 90, it is also possible that the fluid container 90 is separately delivered to the user, and the user attaches the fluid container 90 to the micro pump module 60 after injecting the fluid such as the medicinal liquid in the fluid container 90.

Subsequently, a method of setting and inputting the ejection data to the fluid transportation device by the user and a drive method will be explained with reference to the drawings.

Figure 11:
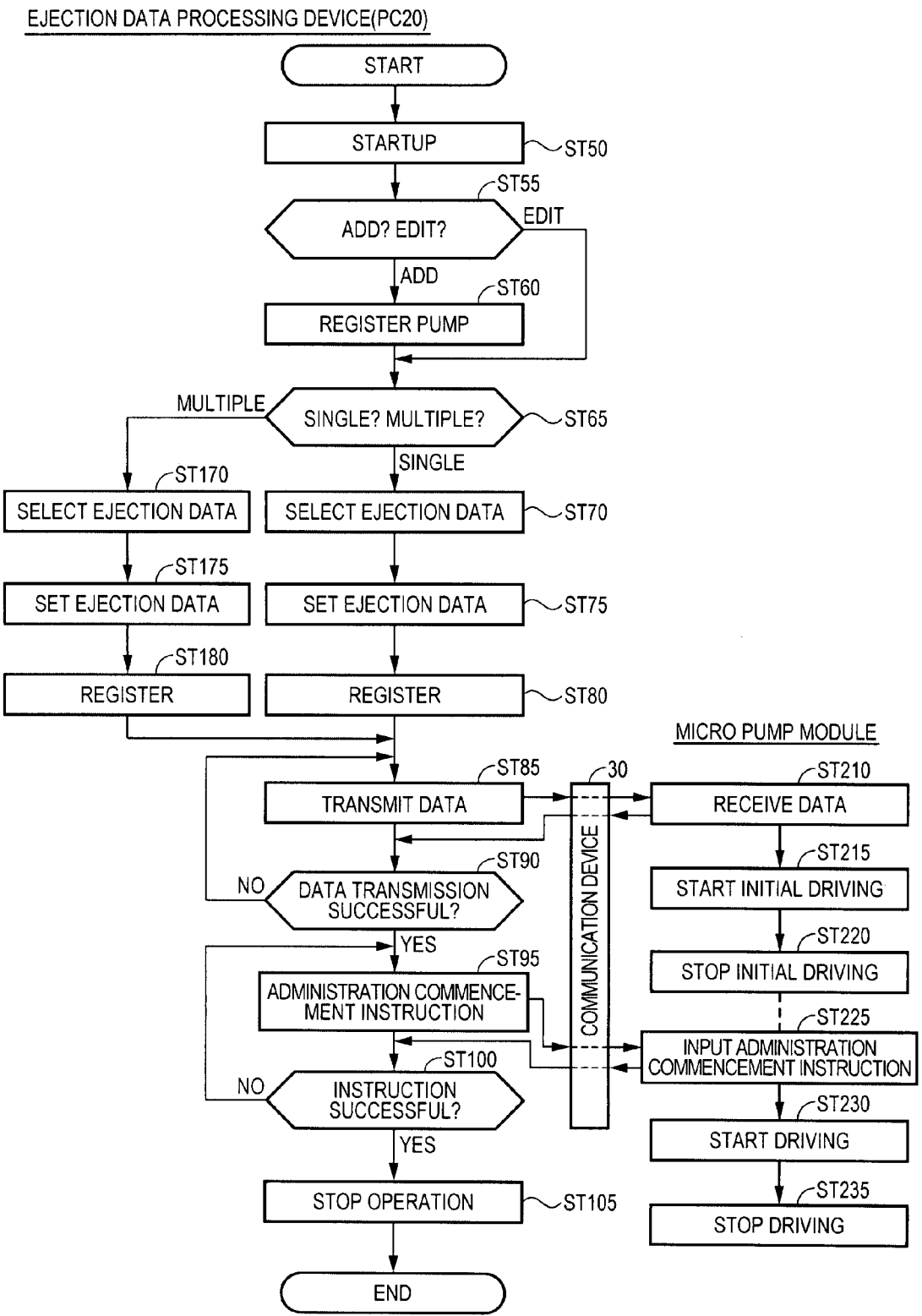
FIG. 11 is an explanatory diagram showing flow of ejection data setting and micro pump module driving according to the embodiment of the invention.

FIG. 11 is an explanatory diagram showing the flow of setting the ejection data to the PC 20 as the ejection data processing device and of driving the micro pump module 60. Firstly, the user inserts the CD-ROM which is supplied from the manufacturer, and to which the software for the ejection data processing device and the fundamental data are written, to the PC 20 to start the software for the ejection data processing device (ST50).

When the software for the ejection data processing device is started, the "Startup screen" shown in FIG. 12 is displayed. On this occasion, whether new ejection data is additionally registered or the registered ejection data is edited is selected (ST55). If "Add" is selected, then "Micro pump module name & code input" screen shown in FIG. 17 is displayed. When the micro pump module name and the code are registered (ST60) and the "OK" button is clicked, "Micro pump control" screen shown in FIG. 14 is displayed.

The micro pump module name is an individual identification appellation of the drive target, and the code is "0503311000" shown as an example in the present embodiment. This code denotes the manufacturing date of Mar. 31, 2005 and the correction coefficient of 1000. Regarding the manufacturing date, when the micro pump module 60 is assembled, the battery 58 is also attached. Therefore, since a part of the drive control circuit 57 start driving to consume the battery power, the description of the manufacturing date becomes necessary.

Figure 14:
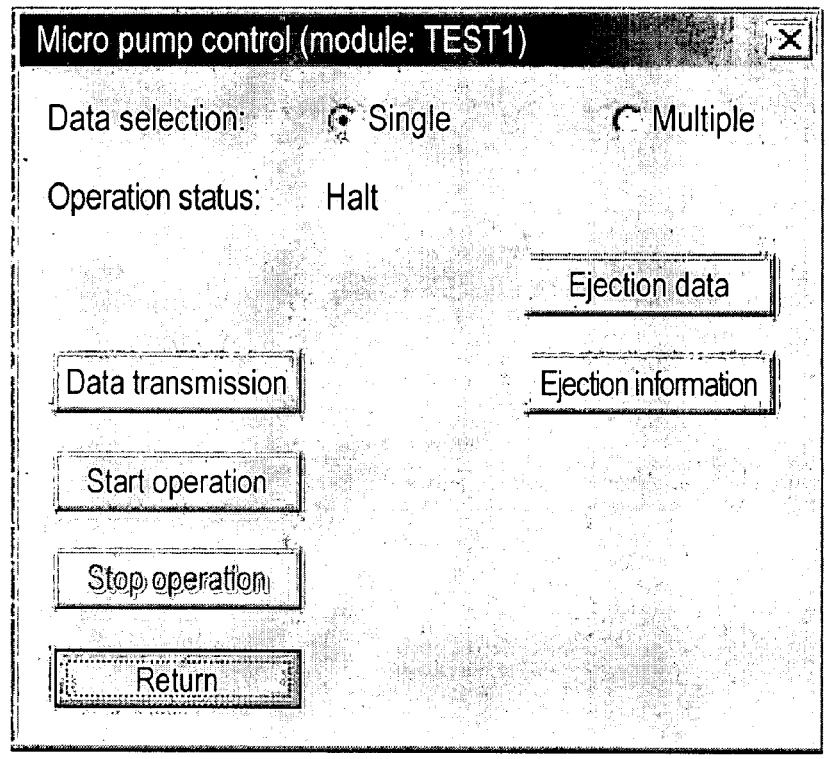
FIG. 14 is an explanatory diagram showing "micro pump control screen" according to one embodiment of the invention.

When "Edit" is selected, "Micro pump control" screen shown in FIG. 14 is displayed, and thereafter, the registration of the ejection data is performed with the same flow as in the case with selecting "Add."

Subsequently, whether the micro pump module to be driven is single mode (single) or multiple mode (multiple) is selected (ST65). Firstly, data setting flow of the case in which "single" is selected will be explained. When the "ejection data" button is selected (ST70) and clicked, "Ejection data setting (single)" screen shown in FIG. 18 is displayed, and the ejection data should be set in this display screen (ST75).

It should be noted here that "Single" denotes that one micro pump module is driven based on one kind of ejection data, while "Multiple" denotes that one micro pump module is driven based on a plurality of kinds of ejection data.

Figure 18:
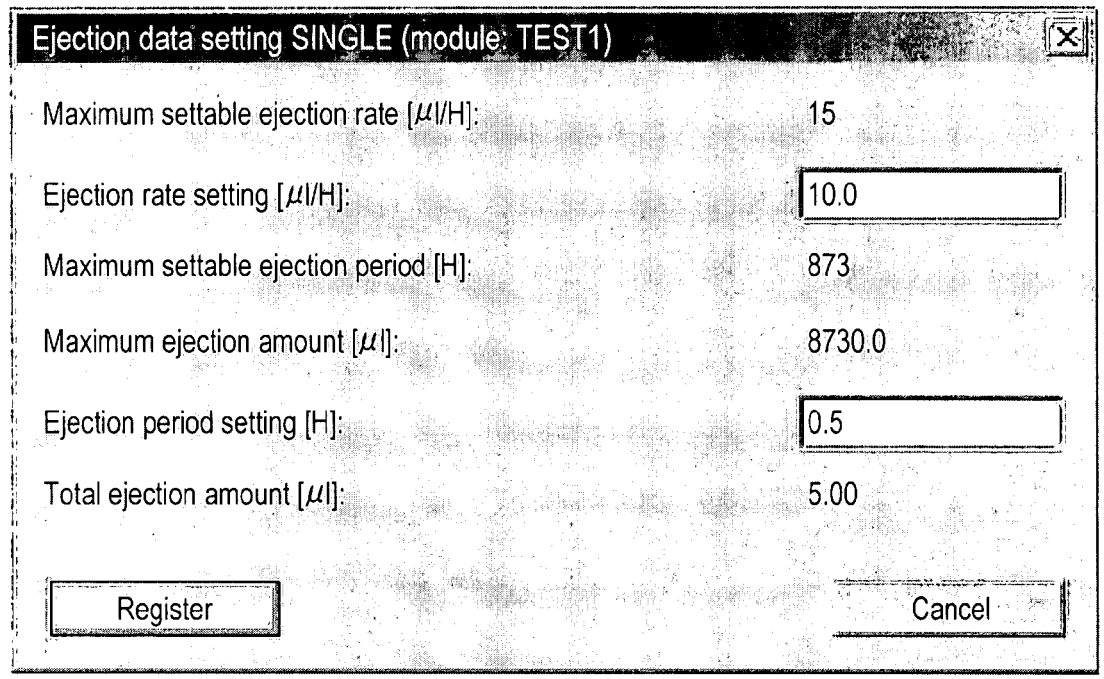
FIG. 18 is an explanatory diagram showing "ejection data (single) setup screen" according to one embodiment of the invention.

FIG. 18 is a screen showing the "Ejection data setting." Explanations will be added regarding the parameters of the ejection data to be set in this screen. "Maximum settable ejection rate [μl/H]" is calculated from the fundamental data input by the manufacturer side. The user should firstly input a necessary ejection rate for use of actual driving in the "ejection rate setting [μl/H] " box. If a numeral exceeding the maximum ejection rate is input as the ejection rate, "Error" is displayed, and in that case, a numeral within the range should be retyped.

"Maximum settable ejection period [hour (H)]" is a value obtained from the battery capacity, the safely ratio, and the total current consumption input as the fundamental data, and "Maximum ejection amount [μl]" is a value obtained from the product of the maximum ejection rate and the maximum ejection period described above, both being calculated by the arithmetic and logical unit of the PC 20.

Then, a predetermined ejection period (driving period) should be set in the "ejection period setting [H]" box. If a value exceeding the maximum ejection period is set, "Error" is displayed, and retyping should be performed.

"Total ejection amount [μl]" is a value obtained from the ejection rate and the ejection period.

When the "Registration" button is clicked after setting and inputting the ejection data described above, the parameters shown in FIG. 18 are stored (ST80), and "Micro pump control" screen shown in FIG. 14 is displayed. On this occasion, the micro pump module 60 is mounted on a predetermined position of the communication device 30, the communication device 130, or the communication device 230, and the communication between the communication device and the micro pump module 60 is established.

Figure 19:
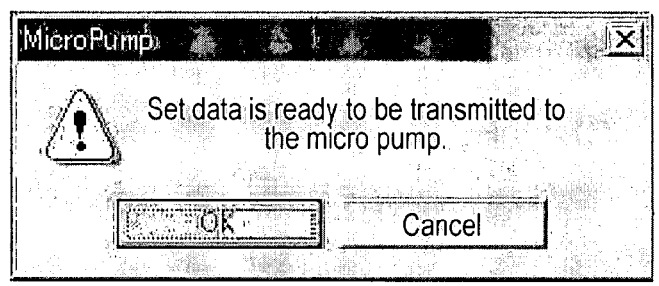
FIG. 19 is an explanatory diagram showing "ejection data transportation screen" according to one embodiment of the invention.

In the "Micro pump control" screen shown in FIG. 14, when the "Data transmission" button is clicked, a screen with "Set data is ready to be transmitted to the micro pump" shown in FIG. 19 is displayed. In this screen, when the "OK" button is clicked, the fundamental data and the ejection data for single data operation are transmitted to the micro pump module 60 (ST85).

In the micro pump module 60, the fundamental data and the ejection data are input (ST210). On this occasion, if it is confirmed that the ejection data thus input includes predetermined contents, a data input completion signal is output to the PC 20 via the communication device 30, the communication device 130, or the communication device 230.

The PC 20 judges whether or not the data transmission has been successful (ST90). If the input completion signal is not input within a predetermined period of time, it is judged that the data transmission has failed, and the "data transmission" operation is performed again.

When the data is input to the micro pump module 60, the micro pump module 60 starts an initial operation (ST215), and after operating in accordance with the fundamental data and the ejection data thus input for a certain period of time, it stops operating (ST220). The initial operation period is previously determined by the fundamental data as described above, and is set as a period from when the assemble of the micro pump module 60 has been completed to when the micro pump module 60 becomes ready to emit the fluid.

Figure 20:
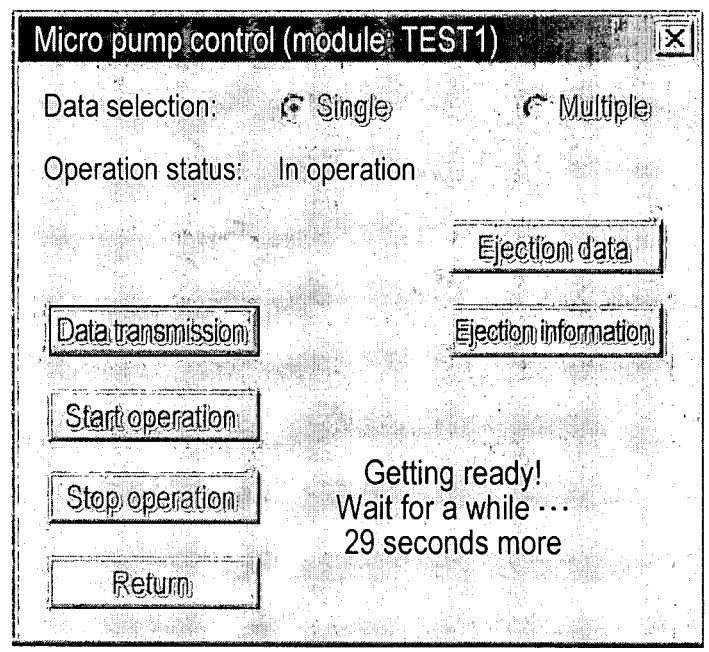
FIG. 20 is an explanatory diagram showing "micro pump control screen" in an initial drive period according to one embodiment of the invention.
Figure 21:
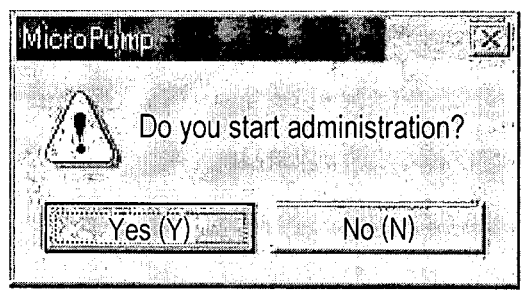
FIG. 21 is an explanatory diagram showing "administration commencement screen" according to one embodiment of the invention.

While the initial operation is performed, the "Micro pump control" screen shown in FIG. 20 is displayed on the PC 20, "In operation" is displayed during the initial operation, and remaining period of time of the initial operation is displayed. When the initial operation is completed, a screen with "Do you start administration?" shown in FIG. 21 is displayed. On this occasion, if "Yes (Y)" button is clicked, the administration commencement instruction is issued (ST95). The administration commencement instruction is transmitted to the micro pump module 60 via the communication device. When the instruction is input (ST225), the micro pump module 60 outputs an instruction input completion signal to the PC 20.

Figure 22:
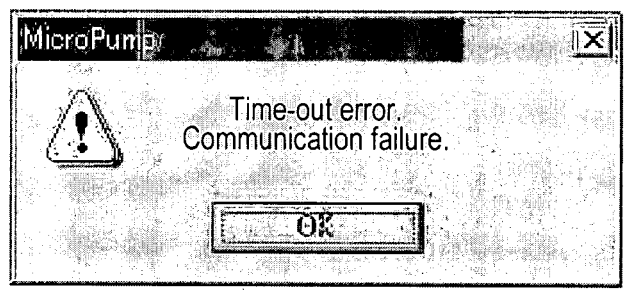
FIG. 22 is an explanatory diagram of "screen showing data transmission failure" according to one embodiment of the invention.

The PC 20 judges whether or not the administration commencement instruction has been transmitted to the micro pump module 60 (ST100), and when the instruction input completion signal is received, the PC 20 waits until the operation of the micro pump module is completed. If the data transmission has failed, the screen shown in FIG. 22 is displayed, and the "OK" button should be clicked to perform the data transmission operation again.

The micro pump module 60, in response to input of the administration commencement instruction, starts the operation (ST230), and operates at the set ejection rate for the set ejection period based on the fundamental data and the ejection data described above, and then terminates (stops) the operation (ST235).

It should be noted that in the case in which the wired communication is used as the communication method, the fluid transportation device 50 is mounted on the predetermined mounting position at this time point. The same applies to the case in which the infrared communication method is adopted.

Further, in the case of the wireless communication method, the administration commencement instruction can be transmitted after the fluid transportation device 50 is mounted on a predetermined position.

The PC 20 also stops the driving count of the PC 20 itself (stop operation; ST105) after the set driving period has elapsed.

It should be noted that after the operation is stopped, when the "ejection information" button is clicked in the "Micro pump control" screen, the ejection information data (driving information) in the actual operation of the micro pump module 60 is displayed on the "Micro pump ejection information" screen shown in FIG. 27.

In this screen, the fact that the single data mode is selected is displayed in the "Micro pump operation data" box, and the reason why the micro pump module 60 has stopped is displayed in the "Micro pump stopping reason." In the drawing, the display of "Time elapsed" denotes that it has stopped after operating for a predetermined ejection period, and if "Low battery voltage" is displayed, it means that the battery voltage is lowered in a shorter period than the predetermined ejection period, and it has stopped in the middle of the operation.

As other ejection information, the "Micro pump driving period [H]" and "Micro pump total ejection amount [µl]" in the actual operation of the micro pump module 60 are displayed.

Figure 23:
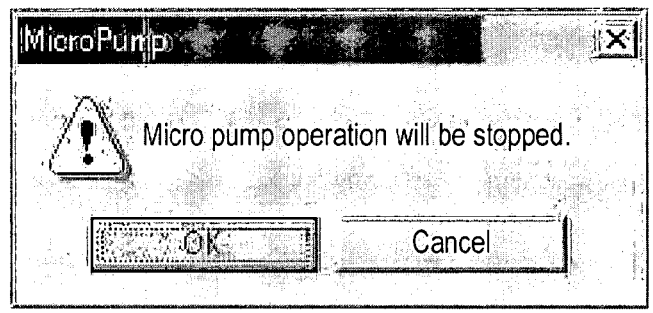
FIG. 23 is an explanatory diagram showing "micro pump operation stop instruction screen" according to one embodiment of the invention.

If the micro pump module 60 needs to be stopped during the operation, in the micro pump control screen shown in FIG. 14, the fluid transportation device 50 is mounted on the communication device 30, the communication device 130, or the communication device 230, and the "Stop operation" button should be clicked. On this occasion, a screen for stopping the micro pump operation shown in FIG. 23 is displayed, and when the "OK" button is clicked, the micro pump operation stopping instruction is transmitted to the micro pump module 60.

It should be noted that if the wireless communication is used as the communication method, it is possible to click the "Stop operation" button to stop the operation while the fluid transportation device 50 is mounted on the predetermined position.

Figure 24:
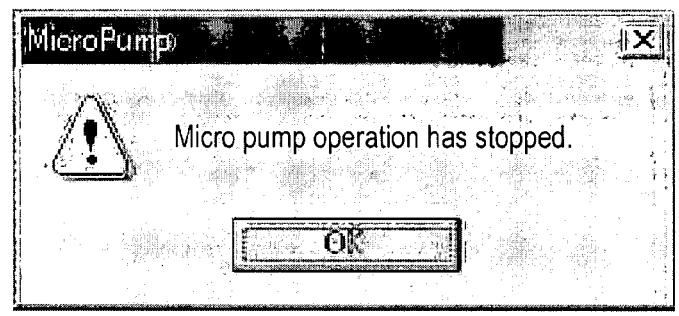
FIG. 24 is an explanatory diagram of "screen showing micro pump operation stop" according to one embodiment of the invention.

When the micro pump stopping instruction is input to the micro pump module 60, a screen of stopping the micro pump operation shown in FIG. 24 is displayed. On this occasion, by clicking the "OK" button, the operation of the micro pump module 60 and the drive count operation (driving) of the PC 20 are terminated.

Figure 25:
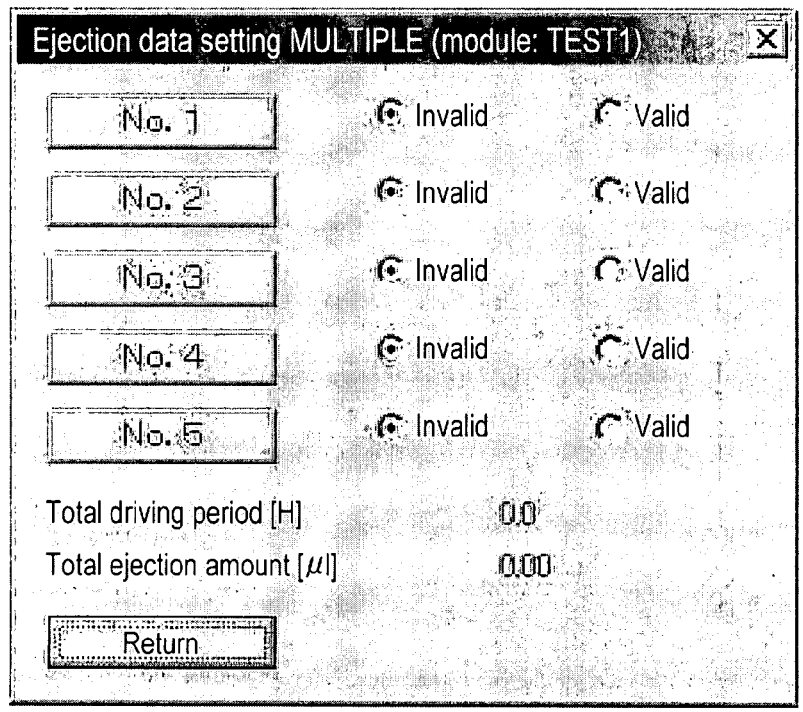
FIG. 25 is an explanatory diagram showing "ejection data (multiple) setup screen" according to one embodiment of the invention.

Then, the multiple mode driving will now be explained. When the "Multiple" driving is selected (ST65) and the "Ejection data" is selected (ST170) in the "Micro pump control" screen shown in FIG. 14, "Ejection data setting (multiple)" screen shown in FIG. 25 is displayed. In this screen, the ejection data for each micro pump module name is set.

The multiple driving denotes that driving with a plurality of kinds of ejection data (ejection condition) is executed on one micro pump module.

In the example shown in FIG. 25, five kinds of multiple data can be set. For example, in order for setting the ejection data of the multiple data No. 1, "No. 1" button should be clicked. Then, "Ejection data setting: multiple data No. 1" shown in FIG. 26 is displayed. The ejection data is set in this screen in the same manner as in the case with the single driving (ST175).

Regarding the multiple data, the ejection data setting screen is common to the multiple data No. 1 through No. 5. Each of the multiple data No. 1 through No. 5 is selected sequentially from the upper column in FIG. 25, and the ejection data therefor is set in the screen shown in FIG. 26. When the setting of the multiple data No. 1 is completed, the radio buttons on the side of the "No. 1" indication are switched from invalid to valid to indicate that the setting of the multiple data No. 1 has been completed, thus enabling setting of the ejection data for the multiple data No. 2. In this way, the ejection data for the multiple data No. 1 through No. 5 is set sequentially.

After setting the ejection data, the "Registration" button is clicked to register the ejection data for the multiple driving (ST180). After the registration, the operation of data transmission is performed in the same manner as the case with the single driving along the following steps of ST85 through the end of driving (ST105), and the micro pump module continues the operation to ST235.

In an example of the multiple driving, the five kinds of ejection data of No. 1 through No. 5 are set for the single micro pump module, and in accordance with the driving start instruction, driving is performed based on the ejection data No. 1, and subsequently, driving is performed based on the ejection data No. 2. In the same manner, driving is performed based sequentially on the ejection data No. 3 through No. 5. The ejection data is set within the ranges of the maximum driving period and the maximum ejection amount.

It should be noted that the ejection information of the micro pump module 60 can be obtained also in the multiple driving mode. Similarly to the single driving mode, when the "Ejection information" button is clicked after "Multiple" is selected in the "Micro pump control" screen shown in FIG. 14, the "Micro pump ejection information" screen shown in FIG. 27 is displayed, and the ejection information of the target micro pump module is displayed. On this occasion, "Multiple data" is displayed in the column of "Micro pump operation data."

Therefore, according to the fluid ejection amount setting method in the fluid transportation system 10 of the embodiment of the invention described above, since a plurality of driving pulse frequencies and widths of the stepping motor is set, the ejection amount per unit time (the ejection rate) and the pulse width of the fluid can be selected by selecting the drive pulse condition. Therefore, the rotational torque of the stepping motor can be set optimally, thus the driving is possible with the optimal conditions selected corresponding to the driving characteristic of the stepping motor in addition to the driving load and the battery capacity. Thus, there can be obtained the advantage that the desired ejection amount and ejection rate can be set, thereby adjusting the ejection amount of a small amount of medicinal liquid and so on.

Further, since the driving condition input to the micro pump module 60 includes the fundamental data set previously, and the ejection data for each of the micro pump modules as the driving targets set prior to driving, and the system sets the fundamental data and the ejection data separately, setting errors or inputting errors can be eliminated.

Further, in the fluid transportation devices for transporting (emitting) the fluid by squeezing the tube, the ejection amount of the fluid is proportional to the rotational speed of the stepping motor, and is proportional to the square (the cross-sectional area) of the diameter of the fluid flowing section of the tube 62. In the rotational speed of the stepping motor, there is caused no difference among the individual fluid transportation devices by previously setting the rotational speed. However, in the diameter of the tube, there is caused a variation in the manufacturing process, and in particular the difference among the production lots is often caused.

In the case of making a small amount of medicinal liquid flow as in the embodiment of the invention, the influence of the difference in diameter of the tube 62 to the ejection amount becomes a substantive level. For example, in the tube with a diameter of 0.5 mm, if the diameter becomes 0.02 mm larger, the difference of about 8% should be caused in the ejection amount per unit time. Therefore, by setting the ejection data in accordance with the diameter of the tube 62, the accurate ejection amount free from the variation in the diameter of the tube 62 can be assured.

Further, since the individual correction coefficient is calculated from the ratio between the reference tube diameter and the diameter of the tube as the driving target, and the ejection data is set for each of the fluid transportation devices to be the driving target, the accurate ejection amount free from the influence of the variation in the diameter of the tube can be obtained.

Further, it is generally known that the variation in the diameter of the tube is caused among the production lots. Therefore, by setting the correction coefficient for each of the production lots, it is possible to eliminate the influence of the variation in the diameters of the tubes.

Further, since the drive control circuit 57 is provided with the power supply voltage detection circuit for detecting the voltage of the battery 58, the battery voltage is detected by the power supply voltage detection circuit to cope with the voltage drop when the remaining power is coming closer to the exhaustion or the variation in the voltage characteristics, and when the voltage becomes lower than the predetermined drive voltage in a range in which the desired ejection amount can be obtained, the driving of the stepping motor is stopped, thus the ejection amount of the fluid can be controlled.

As described above, in the micro pump module 60, in addition to the single driving mode for driving one fluid transportation device with one kind of ejection data, the one fluid transportation device can be driven while switching a plurality of kinds of ejection data (driving conditions). In the multiple driving mode, for example, such a driving mode becomes possible that the ejection rate in one hour after commencement of the driving is set high, the ejection rate in the next one hour is set lower, and in the next one hour the ejection rate is restored to the ejection rate in the beginning of the driving. Thus, assuming that a living-body test for a development of a new drug is executed, the relationship between the administration of the medicinal liquid and the administration rate can sensitively be recognized.

Further, since the ejection information data in driving the micro pump module 60 is input to the PC 20 via the communication device 30, the set ejection data and the ejection information data in actually driving the micro pump module can be compared with each other, thus the driving management of the micro pump module 60, namely the management of the ejection amount can be performed.

The ejection information data described above includes the stopping reason of the micro pump module 60 and the driving period, thus the actual operation status can be confirmed. Regarding the stopping reason of the micro pump module 60, whether the battery voltage has been lowered or any other driving error has been caused in the fluid transportation device can be judged, and further, since the total ejection amount can be calculated from the set ejection data and the actual driving period, the management of the fluid transportation device can appropriately be performed.

It should be noted that the invention is not limited to the embodiment described above but includes modifications and improvements in a range where the advantages of the invention can be achieved.

For example, although in the present embodiment of the invention the PC 20 is adopted as the ejection data processing device, the PC is not a limitation, it is possible to form a system provided with an ejection data processing device dedicated to the present system and equipped with a display section and an operation section.

Further, the fluid transportation device of the present embodiment is small in size, and therefore, can be mounted inside or outside the various mechanical devices, and can be applied to transportation and/or ejection of the various kinds of fluids described above. On this occasion, by using the wireless communication method is used for the communication device, it becomes possible to change the driving condition or confirm the driving status of the fluid transportation device which is placed at a position to which the user hardly reaches with the hand, thus the fluid transportation system can be adopted in various fields corresponding to various use environments.

It should be noted that the setting method of the fundamental data, ejection data, and the ejection amount in the fluid transportation system according to the embodiment described above is only an example, and the order, the range of setting by the manufacturer, and so on can be changed in accordance with the actual usage of the fluid transportation system.

Further, although in the embodiment described above, the micro pump module 60 capable of ejecting only a small amount of fluid is adopted, the present fluid transportation system can be applied to a fluid transportation device for large ejection amount.

Further, although the peristaltic micro pump module is adopted by the fluid transportation system of the present embodiment, other types of small pumps capable of ejecting a small amount of fluid can also be adopted. In such a case, the parameters included in the fundamental data or the ejection data should be set in accordance with the adopted pump.

What is claimed is:

1. A fluid transportation system comprising:
   a fluid transportation device including:
      a flexible tube, a pump unit that ejects a fluid by squeezing the flexible tube,
      a communication section, and
      a battery; an ejection data processing device including:
      an input device that inputs to the fluid transportation device driving condition data that ejects a desired ejection amount of the fluid, the driving condition data including a plurality of different ejection data sets including a first ejection data set having first fluid flow per unit time data and a first driving period and a second ejection data set having second fluid flow per unit time data and a second driving period, the plurality of different ejection data sets being input prior to driving the fluid transportation device; and
a display section that displays at least the driving condition data; and
a communication device that connects the fluid transportation device and the ejection data processing device to each other,
wherein the fluid transportation device is driven based on the first flow per unit time data for the first driving period and, sequentially after the first driving period, driven based on the second flow per unit time data for the second driving period.

2. The fluid transportation system according to claim 1, wherein the communication device is a wireless communication device, and
the communication device includes at least an antenna, and a transmission/reception switcher, and the communication section includes an antenna, and a transmission/reception switcher.

3. The fluid transportation system according to claim 1, wherein the communication device is an optical communication device,
the communication device includes at least a light receiving element, a light emitting element, a light reception control circuit, and a light emission control circuit, and
the communication section includes a light emitting element and a light receiving element respectively opposed to the light receiving element and the light emitting element, a light emission control circuit, and a light reception control circuit.

4. The fluid transportation system according to claim 1, the communication device being a wired communication device, further comprising:
a seal member formed of an elastic body and attached to a chassis of the fluid transportation device; and
a connection terminal implanted to the communication device to stand, and provided with a needle section formed at an end of the connection terminal,
wherein the needle section pierces the seal member and the connection terminal is connected to the connection terminal of the fluid transportation device when the fluid transportation device is mounted on the communication device, and when the fluid transportation device is detached from the communication device, the connection is released and the seal member is closed by the elasticity of the seal member.

5. The fluid transportation system according to claim 1, wherein a chassis forming the fluid transportation device has a projection-less outer shape, and the chassis and the tube are made of a biocompatible material.

6. The fluid transportation system according to claim 1, wherein the fluid transportation device is sealed except an inlet and outlet of the tube.

7. The fluid transportation system according to claim 1, wherein the ejection data processing device includes a section that selects one of a single driving mode that drives the pump unit with a single kind of ejection data, and a multiple driving mode that drives the pump unit with a plurality of kinds of ejection data while switching the plurality of kinds of ejection data.

8. The fluid transportation system according to claim 1, the communication device being a wired communication device, further comprising:
a seal member formed of an elastic body and attached to a chassis of the fluid transportation device;
a first connection terminal provided to the seal member and that connects the inside and the outside of the seal member; and
a second connection terminal provided to the communication device,
wherein the first and second connection terminals are connected to each other when the fluid transportation device is mounted on the communication device, thereby connecting the communication device and the fluid transportation device to each other.

9. The fluid transportation system according to claim 8, wherein the seal member is mainly composed of an outer periphery fixing section fixed to the chassis of the fluid transportation device, a connection terminal fixing section to which the first connection terminal is implanted to stand, an elastic section connecting the outer periphery fixing section and the connection terminal fixing section.

10. The fluid transportation system according to claim 1, wherein the driving condition data input to the fluid transportation device includes fundamental data set initially and ejection data of individual fluid transportation device as a driving target set prior to driving the pump unit, and the fundamental data and the ejection data are set separately.

11. The fluid transportation system according to claim 10, wherein the fluid transportation device is driven with an initial driving term in which the fluid transportation device is driven based on an initial ejection rate and an initial driving period until the ejection of the fluid is started, and an effective driving term following the initial driving term.

12. The fluid transportation system according to claim 1, wherein the ejection data is set in accordance with an individual difference in the diameter of a fluid flowing section of the tube, thereby controlling the ejection amount of the fluid.

13. The fluid transportation system according to claim 12, wherein a correction coefficient is calculated from a ratio between a reference value of the diameter of the fluid flowing section of the tube in the driving condition of the fluid transportation device as a reference and the diameter of the fluid flowing section of the fluid transportation device as the driving target, and
the ejection data of the fluid transportation device is set in accordance with the correction coefficient to correct the ejection amount of the fluid of the fluid transportation device so as to be the same as the ejection amount of the fluid of the fluid transportation device as the reference.

14. The fluid transportation system according to claim 1, wherein ejection information data obtained when the fluid transportation device is driven is input from the fluid transportation device to the ejection data processing device via the communication device.

15. The fluid transportation system according to claim 14, wherein the ejection information data includes at least a stopping reason and a driving period of the fluid transportation device.

16. The fluid transportation system according to claim 1, wherein the pump unit includes at least a stepping motor, a gear train that reduces the rotation of the stepping motor, a drive control circuit of the stepping motor, and the drive control circuit includes a drive pulse setting section that stores a plurality of driving conditions of the stepping motor, and a timer that counts a driving period of the stepping motor, drives the pump unit based on the driving condition data input from the ejection data processing device, and stops the pump unit after a predetermined period of time has elapsed.

17. The fluid transportation system according to claim 16, wherein the reduction ratio of the gear train can be changed by changing an arrangement of the gears of the gear train.

18. The fluid transportation system according to claim 16, wherein the drive control circuit further includes a power supply voltage detection circuit that detects a voltage of the battery, and
the drive control circuit stops the fluid transportation device when a detection value of the power supply voltage detection circuit becomes lower than a predetermined driving voltage of the pump unit.

\* \* \* \* \*